US011844919B2

(12) United States Patent
Lalwani et al.

(10) Patent No.: US 11,844,919 B2
(45) Date of Patent: Dec. 19, 2023

(54) MICRONEEDLE FOR LOCAL DELIVERY OF THERAPEUTIC AGENT

(71) Applicant: THE TRUSTEES OF COLUMBIA UNIVERSITY IN THE CITY OF NEW YORK, New York, NY (US)

(72) Inventors: Anil K. Lalwani, New York, NY (US); Jeffrey W. Kysar, New York, NY (US); Aykut Aksit, New York, NY (US); Daniel N. Arteaga, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 273 days.

(21) Appl. No.: 16/960,033

(22) PCT Filed: Jan. 3, 2019

(86) PCT No.: PCT/US2019/012160
§ 371 (c)(1),
(2) Date: Jul. 3, 2020

(87) PCT Pub. No.: WO2019/136133
PCT Pub. Date: Jul. 11, 2019

(65) Prior Publication Data
US 2020/0345994 A1 Nov. 5, 2020

Related U.S. Application Data

(60) Provisional application No. 62/659,312, filed on Apr. 18, 2018, provisional application No. 62/654,148,
(Continued)

(51) Int. Cl.
*A61M 37/00* (2006.01)
*B33Y 70/00* (2020.01)
*B33Y 80/00* (2015.01)

(52) U.S. Cl.
CPC ... *A61M 37/0015* (2013.01); *A61M 2037/003* (2013.01); *A61M 2037/0023* (2013.01);
(Continued)

(58) Field of Classification Search
CPC ...... A61M 37/0015; A61M 2037/0023; A61M 2037/003; A61M 2037/0046;
(Continued)

(56) References Cited

U.S. PATENT DOCUMENTS 6,045,528 A 4/2000 Arenberg et al.
6,132,755 A * 10/2000 Eicher ............... A61M 37/0015
424/427
(Continued)

FOREIGN PATENT DOCUMENTS

EP 0989868 4/2000
WO 2017/189258 11/2017
(Continued)

OTHER PUBLICATIONS

Faraji Rad Z, Nordon RE, Anthony CJ, Bilston L, Prewett PD, Arns JY, Arns CH, Zhang L, Davies GJ; High-fidelity replication of thermoplastic microneedles with open microfluidic channels; Microsystems & Nanoengineering, 2017, vol. 3, No. 17034.
(Continued)

*Primary Examiner* — Amber R Stiles
(74) *Attorney, Agent, or Firm* — BakerHostetler

(57) ABSTRACT

The disclosed subject matter relates to a cleavable microneedle for delivery of therapeutic agent, wherein the needle includes a longitudinal body having a detachable portion that comprises at least one therapeutic agent. The microneedle may be configured to administer the therapeutic agent to the inner ear of a subject. Also disclosed is a method for preparing a microneedle using two-photon polymerization lithography.

19 Claims, 13 Drawing Sheets

Related U.S. Application Data filed on Apr. 6, 2018, provisional application No. 62/647,216, filed on Mar. 23, 2018, provisional application No. 62/613,162, filed on Jan. 3, 2018.

(52) U.S. Cl.
CPC ............... *A61M 2037/0046* (2013.01); *A61M 2037/0053* (2013.01); *A61M 2037/0061* (2013.01); *A61M 2210/0612* (2013.01); *A61M 2210/0662* (2013.01); *B33Y 70/00* (2014.12); *B33Y 80/00* (2014.12)

(58) Field of Classification Search
CPC .. A61M 2037/0053; A61M 2037/0061; A61M 2210/0612; A61M 2210/0662; B33Y 70/00; B33Y 80/00; B33Y 10/00; A61F 11/00; B29C 64/106; B29C 64/129
See application file for complete search history.

(56) References Cited

U.S. PATENT DOCUMENTS

| | | | |
|---|---|---|---|
| 6,377,849 | B1 | 4/2002 | Enarz et al. |
| 6,611,707 | B1 | 8/2003 | Prausnitz et al. |
| 6,685,697 | B1 | 2/2004 | Arenberg et al. |
| 8,257,324 | B2 | 9/2012 | Prausnitz et al. |
| 8,636,713 | B2 | 1/2014 | Prausnitz et al. |
| 2002/0133129 | A1 | 9/2002 | Arias et al. |
| 2003/0208167 | A1 | 11/2003 | Prausnitz et al. |
| 2004/0106904 | A1* | 6/2004 | Gonnelli ............ A61M 37/0015 604/173 |
| 2005/0209565 | A1 | 9/2005 | Yuzhakov et al. |
| 2006/0195067 | A1 | 8/2006 | Wolter et al. |
| 2006/0264897 | A1 | 11/2006 | Lobl et al. |
| 2007/0038181 | A1 | 2/2007 | Melamud et al. |
| 2007/0078376 | A1 | 4/2007 | Smith |
| 2007/0018543 | A1 | 8/2007 | Etheredge, III et al. |
| 2008/0065002 | A1 | 3/2008 | Lobl et al. |
| 2008/0269685 | A1* | 10/2008 | Singh .................... A61K 9/0021 604/173 |
| 2011/0224629 | A1 | 9/2011 | Jolly et al. |
| 2011/0030685 | A1 | 12/2011 | Darryl et al. |
| 2011/0301681 | A1 | 12/2011 | Risi |
| 2012/0245419 | A1 | 9/2012 | Makower et al. |
| 2013/0331792 | A1 | 12/2013 | Karp et al. |
| 2015/0057604 | A1* | 2/2015 | Arami ................ A61M 37/0015 29/428 |
| 2015/0080802 | A1 | 3/2015 | Kang et al. |
| 2015/0258120 | A1 | 9/2015 | Zarnitsyn et al. |
| 2015/0265824 | A1* | 9/2015 | Lalwani ............ A61M 37/0015 606/186 |
| 2015/0306363 | A1 | 10/2015 | Meyer et al. |
| 2016/0158512 | A1* | 6/2016 | Tamaru ............. A61M 37/0015 604/173 |
| 2016/0361527 | A1* | 12/2016 | Jung ................. A61M 37/0015 |

FOREIGN PATENT DOCUMENTS

| | | |
|---|---|---|
| WO | 2017/195790 | 11/2017 |
| WO | 2017/198872 | 11/2017 |
| WO | 2017/200213 | 11/2017 |
| WO | 2017/204418 | 11/2017 |

OTHER PUBLICATIONS

He M, Yang G, Zhang S, Zhao X, Gao Y; Dissolving microneedles loaded with etonogestrel microcrystal particles for intradermal sustained delivery; J Pharm Sci, Nov. 23, 2017, DOI:https://doi.org/10.1016/j.xphs.2017.11.013.

Van Der Maaden K, Heuts J, Camps M, Pontier M, Van Scheltinga AT, Jiskoot W, Ossendorp F, Bouwstra J; Hollow microneedle-mediated micro-injections of a liposomal HPV E743-63 synthetic long peptide vaccine for efficient induction of cytotoxic and T-helper responses; J Control Release, vol. 269, Jan. 10, 2018, pp. 347-354; epublished Nov. 2017, https://doi.org/10.1016/j.jconrel.2017.11.035.

Hirobe S, Azukizawa H, Hanafusa T, Matsuo K, Quan YS, Kamiyama F, Katayama I, Okada N, Nakagawa S; Clinical study and stability assessment of a novel transcutaneous influenza vaccination using a dissolving microneedle patch; Biomaterials, Jul. 2015, vol. 57, pp. 50-58.

Duan D, Moeckly C, Gysbers J, Novak C, Prochnow G, Siebenaler K, Albers L, Hansen K.; Enhanced delivery of topically-applied formulations following skin pre-treatment with a hand-applied, plastic microneedle array; Curr Drug Deliv, Sep. 2011, vol. 8 / Issue 5, pp. 557-565.

Yu J, Zhang Y, Ye Y, Disanto R, Sun W, Ranson D, Ligler FS, Buse JB, Gu Z; Microneedle-array patches loaded with hypoxia-sensitive vesicles provide fast glucose-responsive insulin delivery, Proc Natl Acad Sci USA, Jul. 2015, vol. 112 / Issue 27, pp. 8260-8265.

Yu J, Zhang Y, Gu Z; Glucose-responsive insulin delivery by microneedle-array patches loaded with hypoxia-sensitive vesicles, Methods Mol Biol, 2017, vol. 1570, pp. 251-259.

Raphael Y, Frisancho JC, Roessler BJ. Adenoviral-mediated gene transfer into guinea pig cochlear cells in vivo. Neuroscience letters 1996; 207:137-41.

Derby ML, Sena-Esteves M, Breakefield XO, et al. Gene transfer into the mammalian inner ear using HSV-1 and vaccinia virus vectors. Hear Res 1999; 134: 1-8.

Komeda M, Roessler BJ, Raphael Y. The influence of interleukin-1 receptor antagonist transgene on spiral ganglion neurons. Hear Res 1999; 131: 1-10.

Wareing M, Mhatre AN, Pettis R et al. Cationic liposome mediated transgene expression in the guinea pig cochlea. Hear Res 1999; 128: 61-9.

Lalwani AK, Han JJ, Walsh BJ et al. Green fluorescent protein as a reporter for gene transfer studies in the cochlea. Hear Res 1997;114:139-47.

Lalwani A, Walsh B, Reilly P et al. Long-term in vivo cochlear transgene expression mediated by recombinant adeno-associated virus. Gene therapy 1998; 5: 277-81.

Jero J, Tseng CJ, Mhatre AN et al. A surgical approach appropriate for targeted cochlear gene therapy in the mouse. Hear Res 2001; 151: 106-14.

ISR and Written Opinion of WIPO Application Serial No. PCT/US2019/012160, dated Mar. 26, 2019.

Extended European Search Report dated Jun. 13, 2016 in Application No. 13862239.4.

International Search Report dated Feb. 24, 2014 in Application No. PCT/US2013/075105.

International Preliminary Report on Patentability dated Jun. 16, 2015 in Application No. PCT/US2013/075105.

Nguyen, Yet al. Cochlear Implant Insertion Forces In Microdissected Humao Cochlea To Evaluate A Prototype Array. Audiology and Neurotology. May 30, 2012; vol. 17, p. 297, col. 2, lines 17-21.

Geerligs, M et al. In Vitro Indentation To Determine The Mechanical Properties Of Epidermis. Journal of Biomechanics. Apr. 7, 2011; vol. 44, No. 6, p. 1178, col. 1, lines 16-25.

Gittard et al.. Two Photon Polymerization of Microneedles for Transdermal Drug Delivery, Expert Opin Drug Deliv., vol. 7, PMC, Apr. 1, 2011.

* cited by examiner

MICRONEEDLE FOR LOCAL DELIVERY OF THERAPEUTIC AGENT

CROSS-REFERENCE TO RELATED APPLICATIONS

This applications claims priority to PCT/US19/12160, filed Jan. 3, 2019, which claims priority to U.S. Provisional Application No. 62/613,162 filed Jan. 3, 2018, U.S. Provisional Application No. 62/647,216, filed Mar. 23, 2018, and U.S. Provisional Application No. 62/659,312, filed Apr. 18, 2018, the contents of each of which are hereby incorporated by reference thereto in their entirety.

GOVERNMENT FUNDING

This invention was made with Government Support under Contract Nos. R01/DC014547-03 awarded by the National Institutes of Health. The government has certain rights in the invention.

COPYRIGHT NOTICE

The disclosure of this document contains material that is subject to copyright protection and all rights are reserved.

FIELD

The disclosed subject matter relates to a microneedle for delivery of therapeutic agents, such as drugs, across anatomic barriers. More particularly, the subject matter relates to a microneedle configured to deliver a precise dosing of therapeutic agent via a detachable portion of the microneedle.

BACKGROUND

An estimated 500 million people worldwide suffer from auditory and vestibular dysfunctions. The underlying causes of many hearing disorders such as sudden or progressive sensorineural hearing loss (SNHL) and tinnitus as well as vestibular disorders such as Meniere's disease manifest themselves within the cochlea (or inner ear). The cochlea is a fluid-filled cavity within the temporal bone of the skull, which is one of the hardest bones in the body. One of the main challenges in treating such auditory and vestibular disorders is the anatomic inaccessibility of the cochlea, which makes it extremely difficult to deliver therapeutics into the cochlea. The development of reliable methods for the precise delivery of therapeutics—including pharmaceutical, molecular and cellular agents—to the inner ear while preserving hearing function and maintaining cochlear architecture remains a formidable challenge in the field of otology.

Delivery of a precise dose of medication across the anatomic barriers, such as for example into the inner ear, is a serious challenge for clinicians. For example, the current methods of therapeutic delivery to the cochlea are inherently imprecise and can result in functional damage to the auditory and vestibular systems. The microneedle embodied herein allows for controlled delivery of therapeutic agents across barrier tissues via temporary microscopic perforations induced by at least one microscopic needle, and the delivery of a cleavable portion of the microneedle body containing a precise amount or dose of therapeutic agent.

Delivery of a precise dose of medication across other anatomic barriers to the Central Nervous System (CNS) is also a serious challenge for clinicians of multiple specialties. Thus, there is a need for a microneedle for local delivery of therapeutic agents across anatomic membranes that is reliable and predictable without promoting anatomic or functional damage.

SUMMARY

In one aspect the disclosed subject matter provides a microneedle comprising a longitudinal body having a detachable portion comprising therapeutic agent. For example, the longitudinal body may have a distal end, a proximal end, and a length therebetween. The detachable portion may be disposed, but not necessarily disposed, at the distal end of the microneedle body. The therapeutic agent can be enclosed within the detachable portion, or coated within or about the detachable portion, or otherwise incorporated with the detachable portion. In some embodiments, the detachable portion comprises biodegradable material, such as biodegradable polymer such that the therapeutic agent is delivered from the detached detachable portion to a subject in a controlled manner. In one embodiment, the microneedles is an array of microneedles.

The microneedle may have a maximum diameter of about 10 to about 150 microns, such as from about 10 to about 50 microns, or from about 10 to about 20 microns, or from about 50 to about 150 microns, or from about 80 to about 120 microns, depending on the application. For example, the size of the microneedle may enable penetration of the round window membrane of the inner ear to create a temporary, self-closing perforation.

The longitudinal body of the microneedle may be hollow or solid, made of silicon or a more rigid material (e.g. a metal such as tungsten) and optionally configured with a taper along at least a portion of its length. The taper may be a gradual taper such as a gradual decrease in diameter along the length of the microneedle, from proximal to distal end. The gradual decrease may be at a constant or variable rate of change to provide a smooth change in diameter. Alternatively, the taper may comprise a stepped taper with one or more abrupt changes in diameter that serve as reinforcing ribs or ledges. In some embodiments, there may be a narrow region of the microneedle at the junction between the distal portion and the proximal portion to facilitate cleavage or detachment of the distal portion from the proximal portion. As used herein, the terms "cleave" and detach" shall be used interchangeably and should be construed as such.

The microneedle may be configured such that the proximal portion comprises a shaft and the distal end comprises a wide base and a narrow tip. The base of the distal portion may comprise one or more projections or barbs that engage the lateral side of the membrane after penetration through the membrane and is held in place thereby. The barb(s) may provide the distal portion with a fishhook-like or arrowhead-like configuration. Retraction of the proximal portion results in cleavage of the distal portion from the proximal portion of the shaft. The distal portion of the microneedle remains on the distal side of the membrane to deliver the therapeutic agent. The proximal portion is removed from the subject's body after cleavage.

Another aspect provides an array comprising one or a plurality of the microneedle described above. The microneedle array can be advanced through and penetrate an anatomic membrane, such as the round window membrane of the inner ear, to create temporary, self-closing perforation(s). The temporary perforations allow access to the inner ear for local drug delivery of therapeutic agents.

The microneedles may be arranged in a regular pattern such as in an ordered array or disordered in a random pattern. Alternatively, the array may be arranged to approximate the shape of a portion of an anatomic membrane such as the round window membrane. In one embodiment, the microneedles are arranged in an array, for example a 10 by 10 array. The size of the array, however, may be dependent on the desired dosage of therapeutic agent. For example, the consistent delivery of therapeutic agent within the biodegradable distal portion by a 10 by 10 array provides a dosage of therapeutic agent that is four times the amount delivered by a 5 by 5 array, and so on.

In another aspect of the disclosed subject matter, a medical device capable of creating temporary perforations in the round window membrane of an inner ear is provided. The medical device includes one or a plurality of the microneedles described above. The microneedle or plurality of microneedles is coupled to, or disposed on, a base, which is configured to physically engage a driver device. Thus, both the medical device and the driver can be separate components that are engageable to each other to define a modular system. Alternatively, the medical device and at least a portion of the driver may be integrated into a unitary or non-separable device.

In another embodiment a system for delivering therapeutic agent to the inner ear of a subject is provided which comprises an instrument for accessing the round window membrane; one or a plurality of microneedles, each microneedle having a diameter of about 10-150 microns with sufficient rigidity to perforate the round window membrane; and a driver, wherein the microneedle or plurality of microneedles is coupled to the driver.

In another aspect, a method of delivering a therapeutic agent through an anatomic membrane is provided which comprises positioning at least one microneedle as described herein proximate the membrane wherein the microneedle is configured to penetrate the membrane; perforating the membrane (to form at least one perforation); and dispensing a therapeutic agent at the perforation(s).

An embodiment provides for delivering a therapeutic agent into the cochlea comprising positioning at least one microneedle as described herein proximate the round window membrane wherein the microneedle is configured to penetrate the round window membrane; perforating the round window membrane (to form at least one perforation); and dispensing a therapeutic agent at the perforation(s).

In another embodiment, the system may further include an indicator disposed along the system, such as a sensor, to indicate when the membrane is fully penetrated by the microneedles. For example and not limitation, a sensor may be included that is capable of sensing penetration into fluid. The sensing of penetration into fluid indicates that the membrane is fully penetrated.

In another embodiment, the system further includes an aspirating lumen within at least one microneedle which is connected to a suction device, e.g. pump or vacuum source. With respect to the aspirating lumen, fluid from the middle or inner ear can be aspirated before, during or after local delivery of therapeutic agent. The system and at least some components can comprise disposable, single-use products.

Thus, described herein is a medical device and system for delivering a therapeutic agent into the cochlea comprising an instrument for accessing the round window membrane, at least one microneedle, the at least one microneedle having sufficient rigidity to perforate the round window membrane (to form at least one perforation), and a delivery mechanism for dispensing a therapeutic agent at the perforation(s).

In accordance with another aspect of the disclosed subject matter, a method of delivering a therapeutic agent into the cochlea is disclosed which comprises providing at least one microneedle on an instrument, positioning the at least one microneedle within the middle ear, perforating the round window membrane (to form at least one perforation), and dispensing a therapeutic agent at the perforation(s).

In another aspect the invention provides a method for preparing a microneedle or a microneedle array comprising one or a plurality of microneedles on a base, the method comprising designing a microneedle configured to penetrate a membrane with a rupture force of from 0.4 to 5 milliNewtons (mN);

configuring a two-photon polymerization lithography apparatus to fabricate the microneedle or microneedle array on a base according to the design; and operating the two-photon polymerization lithography apparatus to prepare the microneedle or microneedle array.

As used herein, configuring the two-photon polymerization lithography apparatus includes aspects of programming the design, setting operating parameters, providing supplies to the apparatus, and any other functions needed to operate the apparatus.

The method can be used to prepare any of the embodiments of microneedle or microneedle array described herein.

In an embodiment, the membrane to be penetrated by the prepared microneedle is a round window membrane.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION

The subject matter presented herein relates to microneedles for addressing the controlled and/or metered introduction of a therapeutic agent, such as a drug, into a patient. Particularly, the presently disclosed subject matter is directed towards an apparatus having one or a plurality of microneedles which allow for reliable and predictable delivery without permanent anatomic or functional damage. For example but not limitation, the microneedle array may be used for delivery of therapeutic agent to the inner ear of a subject.

Figure 1:
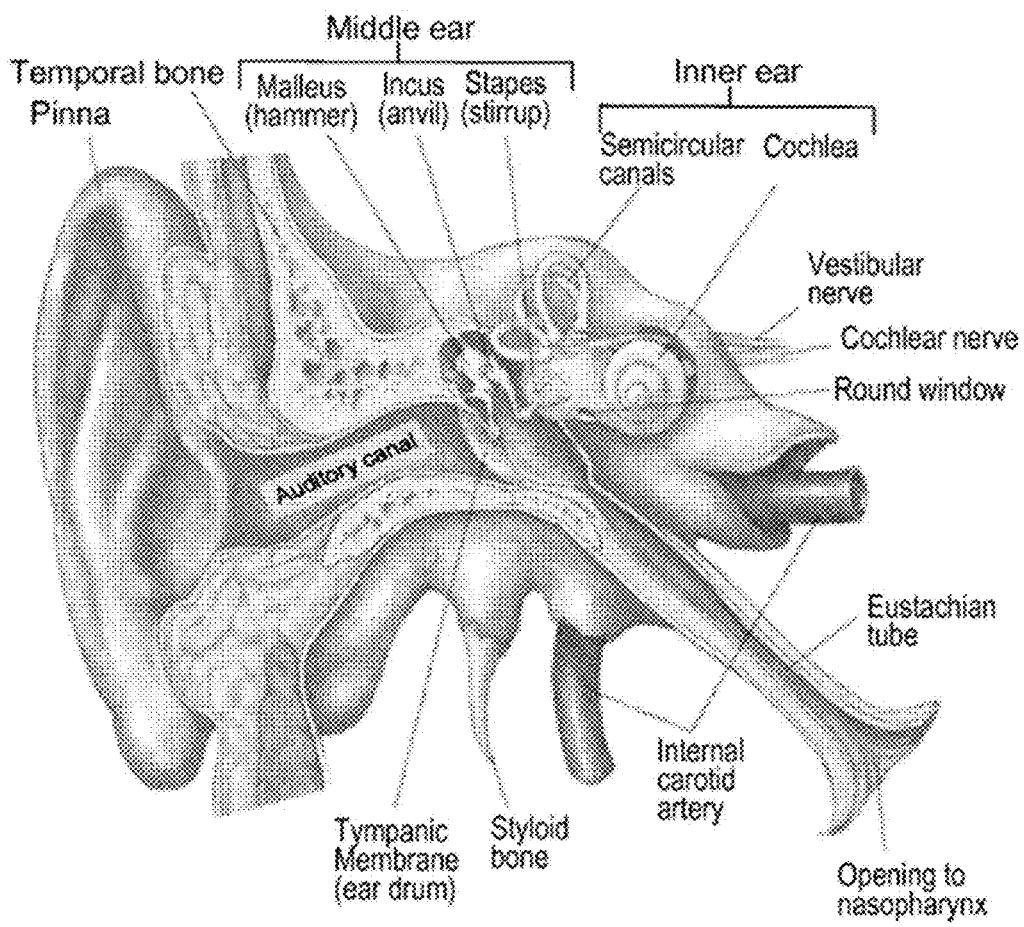
FIG. 1 is a cut-away schematic representation of the ear anatomy.

As shown in FIG. 1, the anatomy of the ear includes a middle ear comprising the hammer, anvil, and stirrup bones, and an inner ear comprising the semicircular canals and cochlea. The middle ear and inner ear have barriers to entry and are separated from the auditory canal by the tympanic membrane or ear drum. Moreover, the inner ear is further protected from entry by its almost impenetrable structure. The round window membrane (secondary tympanic membrane) disposed at the inner ear provides an avenue to permit local delivery of therapeutic agents directly to the inner ear.

Current state-of-the-art treatments intended to deliver therapeutics into cochlea are limited to intratympanic injection of the therapeutic into the middle ear space, after which some of the therapeutic material diffuses across the round window membrane (RWM) into the cochlea. The efficacy of this technique is limited by the unpredictable rate of molecular transport across the RWM. Other methods of direct delivery of therapeutic agents into the cochlea exist, but these techniques breach the inner ear and risk hearing impairment from surgical manipulation and traumatic disruption of the cochlea. Thus, a safe and reliable method for direct and precise intracochlear delivery remains to be developed.

Despite these challenges, the RWM shows promise as a portal for intracochlear delivery. A thin physical membrane that protects the cochlea from middle ear pathology, the RWM displays absorptive capabilities and allows permeation of a large range of materials, including various antimicrobials, steroids and macromolecules. RWM permeability, however, is selective and affected by size, charge, liposolubility and morphology of the compound, as well as RWM thickness. Moreover, the experimental diffusion rate of individual therapeutic reagents across the RWM varies widely from animal to animal, demonstrating a critical need for tools that reduce the variability in molecular transport into the cochlea.

The Round Window Membrane (RWM) is a three layered structure designed to protect the inner ear from middle ear pathology and facilitate active transport. There is an outer epithelial layer that faces the middle ear, a central connective tissue layer, and an inner epithelial layer interfacing with the scala tympani. The most prominent feature of the outer epithelial layer is the extensive interdigitations and tight junctions of its cells; in addition, there is also a continuous basement membrane layer. This architecture with tight junctions and a continuous basement membrane functions as a defensive shield designed to protect the inner ear from middle ear infections. The connective tissue core contains fibroblasts, collagen, and elastic fibers, and houses blood and lymph vessels. The connective tissue is divided roughly into thirds differing in fiber type and density thus essentially establishing a gradient. This layer is responsible for providing compliance to the RWM. Finally, there is a discontinuous inner epithelial layer that bathes in the perilymph of the scala tympani. As previously noted, conventional transtympanic delivery is limited as it relies on the ability of particles to diffuse or be actively transported across this three layered membrane.

A large range of materials are able to cross the RWM, including various antimicrobials, steroids, anesthetics, tracers, albumin, horseradish peroxidase, latex spheres, germicidal solutions, water, ions, and macromolecules (including bacterial toxins) as long as the materials are suitable for simple diffusion transport. Several factors contribute to the RWM permeability, including size, charge, liposolubility, the morphology of the compound, and the thickness of the RWM. Size has proven to be a factor in permeability, as 1 µm microspheres cross the RWM, but 3 µm microspheres cannot. Furthermore, substances with a molecular weight of less than 1000 kDa diffuse across the RWM fairly rapidly, whereas substances over 1000 kDa require pinocytosis to cross the RWM. Charge of the molecule can also impact its ability to traverse the RWM; for example, it has been noted that cationic ferratin crosses the RWM, but anionic ferratin does not. Finally, increased thickness of the RWM will decrease permeability of substances. While the average thickness of the human RWM is between 70 and 80 µm, this thickness can double in inflammatory conditions. RWM permeability can be altered with the use of exogenous adjuvants such as histamine (for its vasodilatory effects), hyaluronic acid (for its proposed osmotic effect), and dimethylsulfoxide (for its ability to increase medication solubility in perilymph); however, their clinical applications are limited. Consequently, a major limitation of conventional transtympanic delivery method that takes advantage of this natural permeability of the RWM is the great variability in intracochlear delivery of the therapeutic agent; this leads to variation in clinical response and toxicity. Furthermore, many therapeutics cannot be delivered due to the molecular size and weight.

Introducing microscopic perforations across the RWM with the goal of enhancing the membrane's permeability to therapeutic materials may help overcome these challenges. Microneedle devices offer an alternative to hypodermic needles for injection of drugs. Microneedles can be designed to penetrate membranes without causing pain. Microneedle arrays have been extensively studied for rapid and painless administration of drugs across the dermis but have not suitable for perforating the RWM. We have demonstrated that microscopic perforations allow for predictable diffusion of materials across the RWM of guinea pigs in vitro. Properly designed microneedles could safely and reliably produce perforations in the RWM to reduce the natural variability in the rate of molecular transport across the RWM. Ultimately, the use of such microneedles may lead to improvements in intratympanic injection delivery that could be accomplished during an office visit.

A challenge for this field is development of low cost manufacturing methods that will lead to clinical translation of microneedle technology. The manufacturing processes commonly used for microneedles fabrication are injection molding, reactive ion etching, chemical wet etching, micromolding. A variety of production methods, including micromachining and direct writing techniques, have allowed for the manufacturing of needles with micro-scale features geared towards drug delivery. They include needle fabrication by the following techniques: micromachining, Electric Discharge Machining (EDM), Selective Laser Sintering (SLS), and Stereolithography (SLA).

Originally developed for use in the semiconductor and microelectromechanical systems (MEMS) industries, multiple micromachining techniques have been successfully utilized in the making of microscopic needles. These methods include isotropic or anisotropic etching of silicon with a photoresist or oxide pattern, etching of glass, and patterning of SU-8. While these methods are highly optimized, inexpensive and readily scalable, they are ultimately limited as they offer little process control and design freedom to engineers utilizing the technology.

Wire Electric Discharge Machining (EDM) uses an electrically charged single-strand of metal wire to machine a metal substrate. When the charged wire approaches the metal substrate, an electrical spark is generated and the resulting process erodes material from the substrate. This method has been used to manufacture micro-scale needles that are sufficiently durable to penetrate human tissue. However needles fabricated via EDM have sub-optimal surface finish and tip sharpness, a limitation that affects most top-down machining methods.

Several direct writing processes have been used to create microscopic needles, all of which use lasers to energize a material and induce reactions that promote binding of the material. Selective Laser Sintering (SLS) uses lasers to heat a metal powder until it melts and re-solidifies into a cohesive durable material. The process starts with a single layer of heat-reactive powder. After the laser finishes tracing the desired pattern on one layer, a new layer of fresh powder is supplied on top of the previously written pattern, the table adjusts its height, and the process is repeated until the sample is complete. The method is limited by the materials it can use, chemical reactions that take place at high temperatures such as oxidation, and the quality of the surface that is created. Similarly, Stereolithography (SLA) utilizes ultraviolet (UV) light to crosslink a photosensitive resin. To begin, a UV laser traces the desired pattern upon the surface of a non-reactive substrate. After the patterning is complete, a fresh layer of resist is placed on the previously written pattern, and the process is repeated until completion of the desired structure. Commercially available SLA type printers do not have sufficient resolution to generate feature sizes in the range that is necessary for microneedles.

The method disclosed herein for producing microneedles suitable for perforating the RWM is 3D direct writing with two-photon polymerization (2PP), a process by which the near-simultaneous absorption of two photons excites and crosslinks a photosensitive resin to generate a durable polymer. As in SLA, a viscous resin, typically a synthetic substance containing acrylate, epoxy, urethane acrylate or vinyl ether functional groups, is placed on a non-reactive substrate. Ultrashort and tightly focused laser pulses are then used to trigger polymerization in an individual voxel of the region to be printed. The focal point then traces the desired pattern voxel-by-voxel until a complex 3-D structure emerges. The nonlinearity of two-photon absorption causes crosslinking of the material to occur within a voxel smaller than the diffraction limit, resulting in superior resolution, approaching the scale of 100 nm. The lasers used in 2PP utilize microscope objectives, thus allowing for easy selection of voxel size of the desired scale. Combining the precision of microtechnology and the design freedom of regular 3D printing, 2PP is the ideal candidate for fabricating polymeric microneedles. As described further herein, we have used micro-scale 3-D printing to create microneedles optimized for RWM perforation.

The systems and methods described below provide a solution to the problem of local drug delivery to the inner ear, which is not limited by factors required for simple diffusion. For example, a perforation of the RWM membrane by a microneedle as disclosed herein has a roughly elliptical shape having a major axis from about 80 to about 100 microns and a minor axis of about 20 to 40 microns. Therapeutic agents having sizes up to about 40 microns, or molecular weights of up to 10,000 kDa can pass through the perforations without being diffusion-limited.

Ultra-high precision 3D molds can be made via 2-photon lithography. Two photon lithography can be used to manufacture molds for making thermoplastic microneedle arrays for drug delivery and fluid sampling across the anatomic membranes the ear, eye and the CNS such as the RWM. Alternatively, microneedles or microneedle arrays themselves may be manufactured directly using 2-photon lithography.

Manufacturing precision microneedle or microneedle array molds using 2-photon lithography allows for each of the following novel improvements to existing needle technology:

Direct manufacturing of slanted or curved needles or needles with complex geometries or base structures for difficult-to-reach anatomic areas;

Injection molding of biodegradable microneedle arrays with barbed or fishhook-style fasteners at the base and/or tip of individual needles, allowing for securely embedding the array within tissue membranes for days/weeks following the implantation and/or hollow or solid needles that detach upon insertion, break down and release contents;

Injection molding of internal reservoirs, either within the body of the needle or the base, to contain a precise amount of pharmaceutical, molecular or cellular therapeutic material and releasing that material into closed anatomical spaces in a controlled manner;

Direct manufacturing of microscopic hollow needles for the controlled delivery of pharmaceutical, molecular or cellular therapeutic materials contained within microscopic capsules.

Figure 3A:
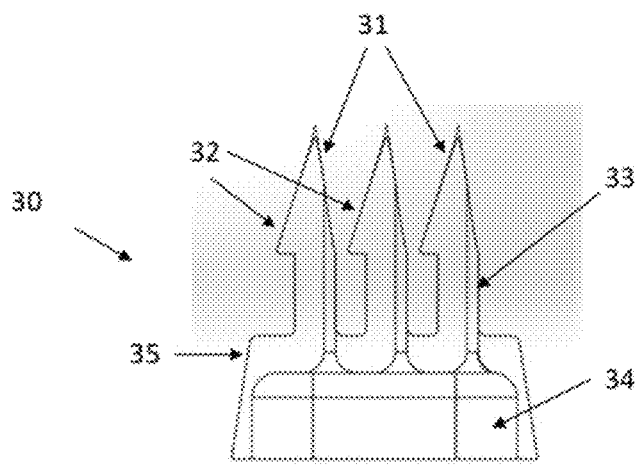
FIGS. 3A and 3B are cross-sectional and perspective images of a design of an array of barbed microneedles on a base according to according to an embodiment of the disclosed subject matter.
Figure 3B:
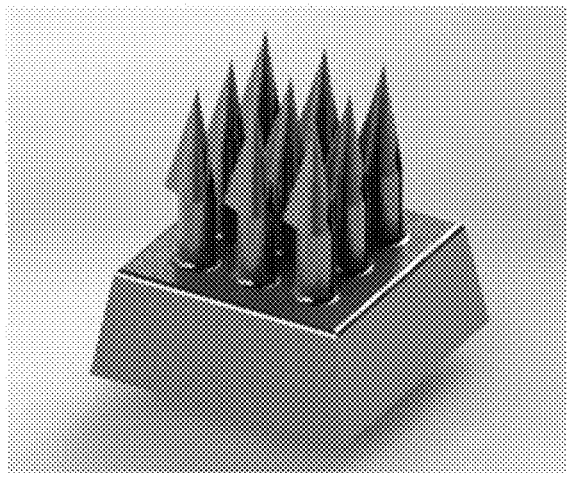

Since the precision of this manufacturing process is very high, very smooth ultra-sharp needles can be made that are specifically engineered to reduce insertion force, minimizing the damage to the membrane and any surrounding tissue. Tip geometry can be characterized as approximating a hemisphere, having a radius of curvature, positioned at the distal end of the microneedle. In one embodiment, the microscopic needles include a tip diameter size of 0.3 to 50 microns (radius of curvature of 0.15 to 25 micron). In other embodiments, the microscopic needles include a tip diameter size ranging from 0.5 to 25 microns (radius of curvature 0.25 to 12.5 microns), e.g., 0.6 to 1.4 microns (radius of curvature 0.3 to 0.7 microns). Notably, the tip diameter is smaller than the diameter of the microneedle shaft, providing a microneedle with a tapered distal end to reduce insertion force. Desirably, the tip geometry is designed to provide a rupture force for the membrane, such as the RWM, of about 0.4 to about 5 mN. One can appreciate that the structure of the membrane to be penetrated may influence the design of the microneedle in terms of its length, cross-section, such as diameter, and/or tip sharpness in order to provide controlled perforation of the membrane so that resulting perforation(s) can self-close or heal after removal of the microneedle. An exemplary microneedle useful for perforating a RWM comprises a shaft having a proximal shaft diameter of 100 microns and a distal portion comprising a gradual taper to a tip having a radius of curvature of about 500 nanometers (0.5 microns). The distal portion may comprise a polygonal shape or complex shape. In some embodiments, such as shown in FIGS. 3A and 3B, the distal end comprises a taper that increases (along the microneedle in the proximal direction) from a small diameter (such as 0.3 micron) at the tip to a cross-section larger than that of the microneedle shaft, providing a barbed distal end. The microneedle array can be embedded in tissue, and release therapeutic agents while slowly decomposing over a period of time, such as hours/days/weeks, leaving behind only microscopic perforations that would quickly heal. This drug delivery method allows physicians to control the amount of the drug administered as well as the rate at which the drug is transported across the membrane by controlling the drug amount in the detachable portion of the microneedle. The detachable portion may comprise a reservoir having a specific drug concentration. As used herein, the term reservoir includes a void, internal space or matrix for holding a therapeutic agent for administration. It may include a coating or other solid form comprising the therapeutic agent on the exterior of the microneedle, or within the microneedle or a portion thereof. The therapeutic agent may optionally be encapsulated in a matrix, such as in microspheres, comprising polymeric material which is preferably biodegradable to release the therapeutic agent at a controlled and/or predictable rate. Depending on the amount of therapeutic agent to be administered and its rate of administration, the reservoir(s) may be located within the microneedle(s), within the base of the microneedle array, or proximally from the microneedle array, such as contained within the body of the medical device, or in a reservoir connected by a lumen through the device to the microneedle array.

Figure 2A:
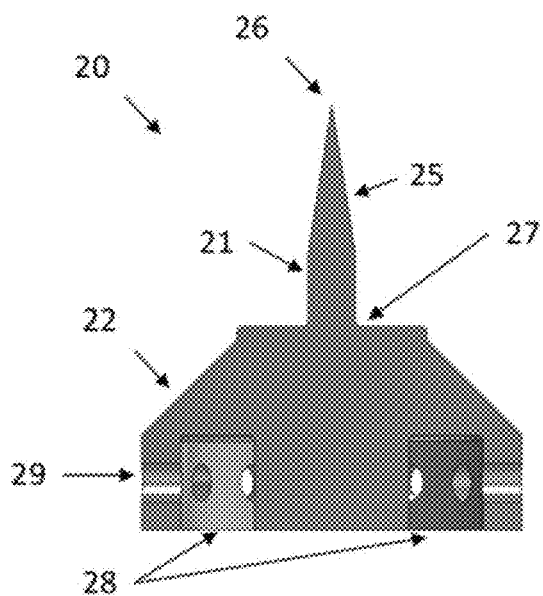
FIGS. 2A and 2B are cross-sectional and perspective representations of an exemplary device having an array of a single microneedle on a base in accordance with some embodiments of the disclosed subject matter.
Figure 2B:

The microneedle array comprises one microneedle, or a plurality of microneedles arranged on a base. A representative design for a microneedle array comprising a single microneedle is shown in FIGS. 2A and 2B. FIG. 2A shows a cross-sectional image of the microneedle design 20 and its base 22. The proximal portion 21 of the microneedle comprises a shaft of constant diameter. The distal portion 25 comprises a tapered portion having gradual taper having a constant rate of decreasing diameter terminating at a needle tip 26 characterized by a radius of curvature that is an indication of its "sharpness". Fillets 27 can be seen at the junction of the proximal portion 21 with the base 22 to reduce possible stress concentrations due to bending. A fillet is a rounding of an interior or exterior corner of a part design. Fillet geometry, when on an interior corner is a line of concave function. An annular hollow 28 in the base 22 is configured to engage the end of a Gauge 23 Blunt Tip Needle. Channels 29 are included to allow drainage of the photoresist after fabrication, as discussed further in the Examples section. The base 22 of the needle 20 can be seen to have the imprint of a Gauge 23 Blunt Tip Needle. FIG. 2B shows a 3D graphical perspective rendering of the design.

Figure 4:
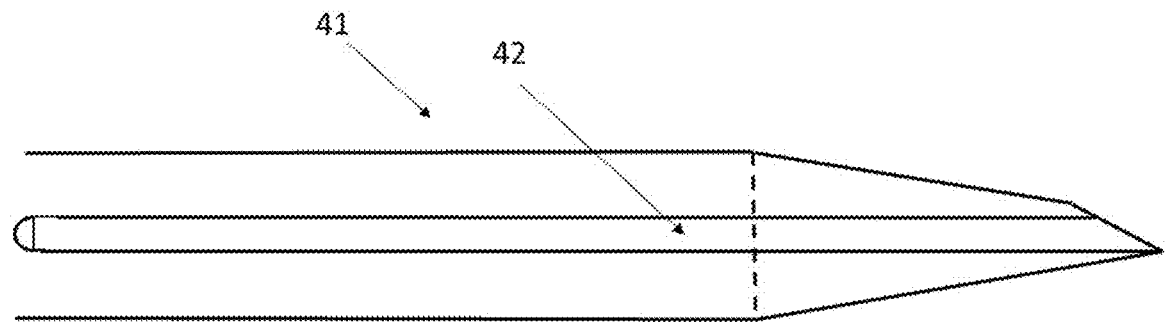
FIG. 4 is a cross-sectional representation of a single microneedle having an internal reservoir for containing a therapeutic agent according to an embodiment of the disclosed subject matter.

Representative images of other microneedle arrays are shown in FIGS. 3A and 3B. FIG. 3A shows a cross-section schematic of a microneedle array 30 wherein the microneedles 31 comprise barbs 32 to engage the membrane after penetration and allow for such a device to be securely embedded in tissue membranes. They also comprise open channels or lumens 33 along one side of each microneedle to transport a therapeutic agent from the reservoir 34 in the base 35 to the distal side of the RWM by, for example, capillary action. FIG. 3B shows a perspective view of a 3 by 3 array of microneedles using the design principles of the microneedles shown in FIG. 3A. FIG. 3A depicts a reservoir 34 for therapeutic agents within the base 25 of the array but reservoirs are not limited to such. The reservoirs could also be located within the bodies of the individual microneedles themselves, as depicted in FIG. 4. FIG. 4 depicts a cross-section of a microneedle 41 comprising a reservoir lumen 42.

In accordance with an aspect of the disclosed subject matter, a device capable of locally delivering a therapeutic agent is provided. The device includes one or a plurality of microneedles configured to controllably penetrate (to a desired depth) an anatomic barrier, such as the inner ear or eye, to create temporary access through temporary perforations. The plurality of microneedles may have a regular or ordered arrangement such as in an array, or have an irregular or random arrangement, if so desired.

The array of microneedles can be mounted onto a surgical instrument (e.g. catheter) that allows access to the RWM either via the tympanic membrane or via the mastoid process. Accordingly, the device includes a base and one or a plurality of microneedles disposed on the base. The base is adapted to mount onto a medical or surgical instrument that allows access to the RWM either via the tympanic membrane or via the mastoid process. In this regard, the base can include threads to screw onto the surgical instrument. However, other structures for physical coupling to the surgical instrument can be employed as would be known to one of skill in the art, such as clips, snap-on friction fit engagement, and the like. Once the microneedles are positioned proximate the RWM, a driver can operate to insert the microneedles into the RWM to create the perforations to the desired depth. As used herein, the driver is a portion of the instrument configured to distally advance the microneedle array from a retracted position to an extended position in which it penetrates the round window membrane. The driver can operate to advance the microneedle array using for example mechanical force, hydraulic force or pneumatic force. Alternatively, the driver can operate electrically, based on passage of electric current through a set of magnetic coils positioned proximal and spaced apart from the shaft of the base of the plurality of microneedles, to advance the microneedles from a retracted position to an extended position. The main shaft of the base of the microneedle array is mounted in linear bearings so as to allow motion of the shaft along its axis, which is effected by the magnetic coils. Thus the position of the shaft is determined and controlled by the electric current flowing through the magnetic coils. Following insertion of the microneedle(s) into the membrane, the driver can be operated to retract from the membrane and either withdraw the microneedles, or leave them or portions thereof in place in the membrane.

The configuration of the microneedle(s) can take a number of different forms as shown schematically in FIGS. 6 through 9. In these Figures, the configurations are conceptual and respective dimensions of the portions of the microneedle are not necessarily to scale. Radii of curvature of microneedle tips and fillets are also not shown. When the microneedle optionally comprises a detachable (distal) portion to be left in the membrane for delivery of a therapeutic agent, it is shown as unshaded and (proximal) portions of the microneedle that are to be removed from the membrane are shown as shaded. Some microneedle embodiments may comprises various combinations of the individual features shown in FIGS. 6 through 9.

For example, the microneedles may comprise stepped tapers with abrupt changes in diameter that serve as reinforcing ribs or ledges. An embodiment of a microneedle with a stepped taper is shown schematically in FIG. 6, in which the proximal portion 61 of the microneedle 60, having a gradual taper (as shown, with constant reduction in diameter), is attached to a base 62. An abrupt change in taper (as shown, the diameter of the microneedle shaft is reduced abruptly at 63) provides a ledge on the microneedle 60. The shaft of the microneedle has a constant (reduced) diameter for a middle portion 64 and the distal portion 65 resumes a gradual taper to the microneedle tip 66. The ledge at 63 may provide a stop that engages the proximal surface of the membrane to limit penetration of the microneedle into the membrane. It may also serve as a reinforcement that engages with the proximal surface of the membrane thereby providing leverage to facilitate detachment of the distal portion 65 from the proximal portion 61 of the microneedle.

In some embodiments, there may be a narrow region of the microneedle at the junction between the distal portion and the proximal end to facilitate cleavage or detachment of the distal portion from the proximal portion. An embodiment of a microneedle with a narrow region is shown schematically in FIG. 7, in which the proximal portion 71 of the microneedle 70 having a constant diameter is attached to a base 72. A narrow region or neck (as shown, the diameter of the microneedle shaft is reduced at 73) and the shaft of the microneedle in the distal portion returns to the larger diameter for a middle section 74 and then resumes a gradual taper at 75 to the microneedle tip 76. The neck 73 provides a weakened region of the microneedle that facilitates fracture of the microneedle at that location.

In some embodiments that employ a solid microneedle construction, the distal end of a proximal portion of the microneedle(s) can be coated with a biodegradable material comprising a therapeutic agent to form a distal portion and permit local delivery of the therapeutic agent. The coating may be configured so that it is releasably adhered to the tip of the proximal end and is held in place by pressure of the microneedle tip against the membrane while the microneedle is driven forward through the membrane. Once the membrane is penetrated, the distal portion engages the membrane and is pulled from the proximal portion as it is retracted. An embodiment comprising this configuration is shown schematically in FIG. 8. In this embodiment, the proximal portion 81 of the microneedle 80 is attached to a base 82. The distal portion 85, comprising the therapeutic agent, of the microneedle 80 may comprise a conic region having a base diameter 87 greater than the shaft diameter of the proximal portion 81, which continues down the outside of the shaft of the microneedle 80, providing a coated region 88 terminating in a flange 83 configured to engage the distal side of the membrane. The proximal portion 81 of the microneedle 80 extends into the interior of the distal portion, shown as the diagonally shaded region 84. In the embodiment shown, the microneedle tip 86 is left uncoated to provide a sharp tip for penetrating the membrane.

Alternatively, the proximal portion of the microneedles may be hollow and a section of the distal portion is inserted into the lumen of the proximal portion. An embodiment of this configuration is shown schematically in FIG. 9A. The microneedle 90a comprises a proximal portion 91a attached to a base 92a. A lumen 94a in the proximal portion 91a can be filled with a distal portion 95a, comprising a therapeutic agent. In the embodiment shown, the lumen 94a is offset from the central axis of the microneedle 90a to provide a solid tip 96a to penetrate the membrane. The distal portion 95a may be configured to extend into the region proximate to the tip 96a and may optionally comprise a flange 93a to engage the distal side of the membrane. After insertion of the distal end of the microneedle and engagement with the membrane, the distal portion 95a can be pulled from the lumen when the proximal portion 91a is retracted. Optionally, the base 92a may comprise a lumen 97a configured to be in communication with lumen 94a. Ejection of the distal portion 95a from the proximal portion 91a can be facilitated by air pressure, fluid pressure, or the action of a piston through the lumen 97a.

Figure 9A:
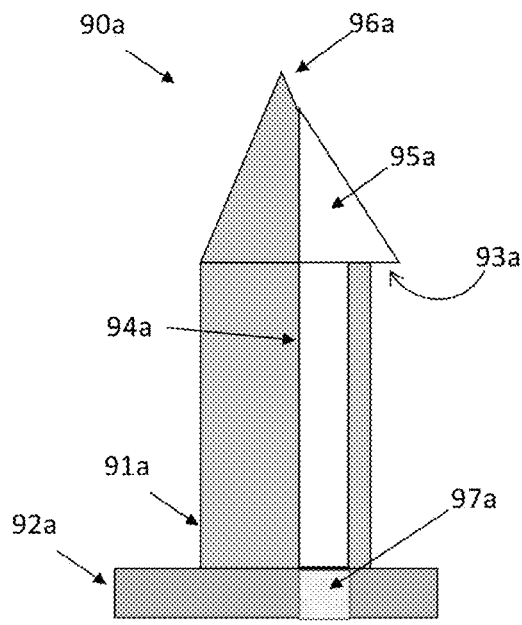
FIGS. 9A and 9B are schematic representations of an exemplary microneedle having a detachable portion positioned in an internal lumen according to an embodiment of the disclosed subject matter.
Figure 9B:
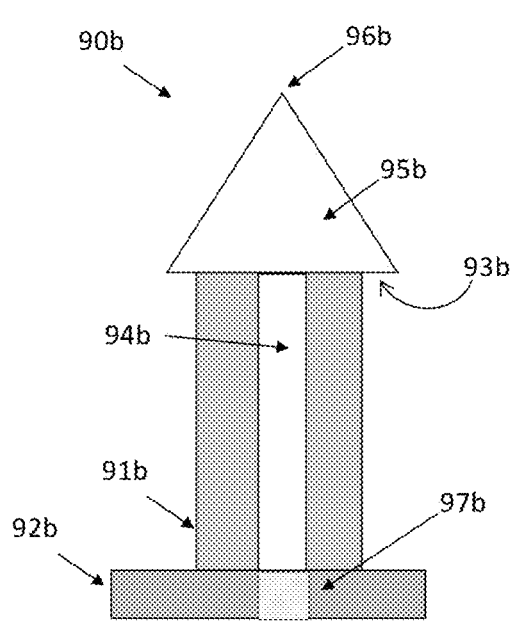

An alternate embodiment of this configuration is shown schematically in FIG. 9B. The microneedle 90b comprises a proximal portion 91b attached to a base 92b. A lumen 94b in the proximal portion 91b can be filled with a distal portion 95b, comprising a therapeutic agent. In the embodiment shown, the lumen 94b is aligned with the central axis of the microneedle 90b to. The distal portion 95b is configured provide a solid tip 96b to penetrate the membrane and may optionally comprise a flange 93b to engage the distal side of the membrane after penetration. After insertion of the distal end of the microneedle and engagement with the membrane, the distal portion 95b can be pulled from the lumen when the proximal portion 91b is retracted. Optionally, the base 92b may comprise a lumen 97b configured to be in communication with lumen 94b. Ejection of the distal portion 95b from the proximal portion 91b can be facilitated by air pressure, fluid pressure, or the action of a piston through the lumen 97b.

In any of the embodiments shown in FIGS. 6 through 9A and 9B, the driver may be configured to tilt the microneedle or microneedle array after insertion of the distal portion and provide a shearing or prying force to facilitate cleavage of the distal portion from the proximal portion.

In some embodiments of a microneedle having an internal or open lumen according to FIGS. 3, 4 and 9A and 9B, the therapeutic agent may comprise a liquid contained within the lumen that can be dispensed after the microneedle penetrates the membrane. In these embodiments, the liquid therapeutic agent may leave the lumen via capillary action into the fluid on the distal side of the membrane, or it can be dispensed with the facilitation of air pressure, fluid pressure, or the action of a piston through the lumen. Alternatively, the microneedle 90a shown in FIG. 9A may be configured without the distal portion 95a in the lumen 94a. In this embodiment, the open lumen, optionally in fluid communication with the lumen 97a, can be used to deliver a fluid therapeutic agent through the membrane after it is penetrated by the microneedle. The therapeutic agent can be contained within the lumen 94a, similar to the microneedle illustrate in FIG. 4. Alternatively, the lumen 94a can deliver a therapeutic agent contained in a reservoir (not shown) in the base 92a of the microneedle or in the body of the medical device via lumen 97a.

The microneedle arrays disclosed herein are designed for administration of therapeutic agents, which can be delivered through perforations in any anatomic barrier. The size of the needle can be varied greatly depending on the tissue and the material to be injected. The microneedles can be formed from a variety of metals and polymers that are biocompatible/degradable. In an exemplary embodiment, the microneedles are formed of silicon due to its relative ease of manufacture. In alternative embodiments, the microneedles can be formed of more rigid materials (e.g. tungsten) which allow for greater loading without buckling or deformation. The application of microneedle arrays to RWM can serve as an agile method for intracochlear delivery.

In some embodiments each microneedle can be formed with a uniform geometry such that each corresponding perforation is a uniform and constant depth. Additionally, or alternatively, select microneedles can be formed with differing geometries to provide a non-uniform or patterned perforation design.

Furthermore, a greater concentration of microneedles can be provided at one portion of the tissue than another to provide the operator with greater flexibility and customization for different patients. Moreover, the microneedles can be formed with differing lengths which coincide or map to the contour of the tissue so as to ensure a uniform depth of insertion into the tissue across a varying or non-planar shape. In other embodiments, the microneedles have substantially the same configuration but are arranged on a base that is contoured to approximate the shape of the membrane that is to be perforated. In an exemplary application, the RWM has a non-planar shape, where microneedle arrays of non-uniform heights would be necessary for simultaneous contact and perforation. The non-uniform height may be realized using microneedles of different lengths or microneedles having the same length arranged on a base with a nonplanar surface.

For example the apparatus for penetrating a membrane may comprise:

a plurality of needles including a first needle and a different second needle, the first needle including a first height and the second needle including a different second height, the first needle and the second needle being configured to (i) penetrate the membrane simultaneously to form a non-uniform design on the membrane, and (ii) penetrate the membrane at a uniform depth of insertion such that the depth of insertion of the first needle including the first height is the same as the depth of insertion of the second needle including the second height.

Embodiments of the apparatus include those wherein the first needle includes a lumen extending from a proximal portion to a distal end of the first needle, the lumen including a reservoir, the reservoir configured to carry a therapeutic agent.

Embodiments of the apparatus include those wherein the second needle includes a lumen extending from a proximal portion to a distal end of the second needle, the lumen including a reservoir for carrying a therapeutic agent.

The apparatus may be configured to selectively retract a first microneedle or a first portion of the plurality of microneedles from the membrane while a second microneedle or a second portion of the plurality of microneedles remains penetrated into the membrane, thereby exposing the microperforation(s) for delivery of a therapeutic agent through the membrane.

In some embodiments, a first microneedle or a first portion of a plurality microneedles may be configured with barbed tips to securely engage the membrane and hold the array in place while a second microneedle or a second portion of the plurality of microneedles are configured to deliver the therapeutic agent(s) by any of the methods described above.

The array of microneedles can be mounted onto a surgical instrument (e.g. catheter) that allows access to the RWM either via the tympanic membrane or via the mastoid process. Accordingly, the device includes a base and one or a plurality of microneedles. The base is adapted to mount onto a surgical instrument that allows access to the RWM either via the tympanic membrane or via the mastoid process. In this regard, the base can include threads to screw onto the surgical instrument. However, other structures for physical coupling to the surgical instrument can be employed as would be known to one of skill in the art, such as clips, snap-on friction fit engagement, and the like. Once the microneedles are positioned proximate the RWM, a driver can operate to insert the microneedles into the RWM to create the perforations to the desired depth. As used herein, the driver is a portion of the instrument configured to distally advance the microneedle array from a retracted position to an extended position in which it penetrates the round window membrane. The driver can operate to advance the microneedle array using for example mechanical force, hydraulic force or pneumatic force. Alternatively, the driver can operate electrically, based on passage of electric current through a set of magnetic coils positioned proximal and spaced apart from the shaft of the base of the plurality of microneedles, to advance the microneedles from a retracted position to an extended position. The main shaft of the base of the microneedle array is mounted in linear bearings so as to allow motion of the shaft along its axis, which is effected by the magnetic coils. Thus the position of the shaft is determined and controlled by the electric current flowing through the magnetic coils.

The plurality of microneedles can be a component device that is configured to engage a surgical instrument for introduction into the ear, such as an introducer, catheter, or other device. As used herein an introducer or catheter is a tubular device configured to position the microneedle array into proximity to the round window membrane. The device may comprise a sheath to contain the microneedle array and other components of the device during insertion through the tympanic membrane or mastoid process. In some embodiments the introducer may comprise a sheath surrounding a more flexible catheter that can advance further toward the RWM. For example, the introducer may be inserted into the auditory canal and penetrate the tympanic membrane into the middle ear, either by directly perforating the tympanic membrane or entering through a previously established opening in the membrane. The introduction may involve making a small incision in the ear canal, i.e., anesthetized tympanic membrane (ear drum) and lifting the ear drum to create an access point to the middle ear. Once the access is available, the medical provider can insert the introducer or catheter into the middle ear, where it can be advanced to a position proximate to the round window membrane.

Figure 5:
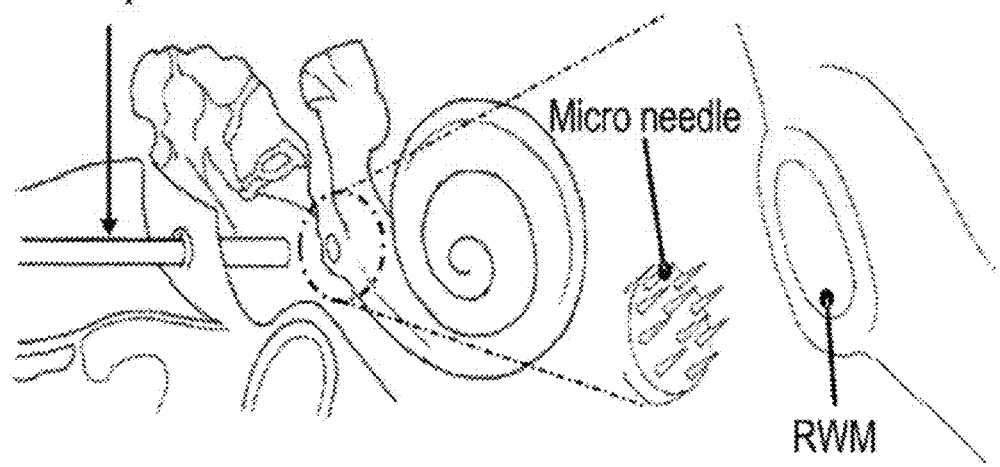
FIG. 5 is a schematic representation of an exemplary device having a plurality of microneedles coupled to a delivery device positioned in proximity to the round window membrane in accordance with according to embodiments of the disclosed subject matter.
Figure 6:
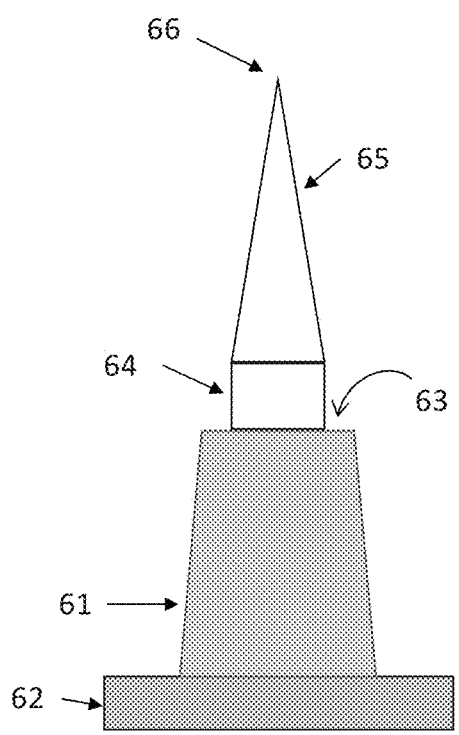
FIG. 6 is a schematic representation of an exemplary microneedle having a stepped taper according to an embodiment of the disclosed subject matter.
Figure 7:
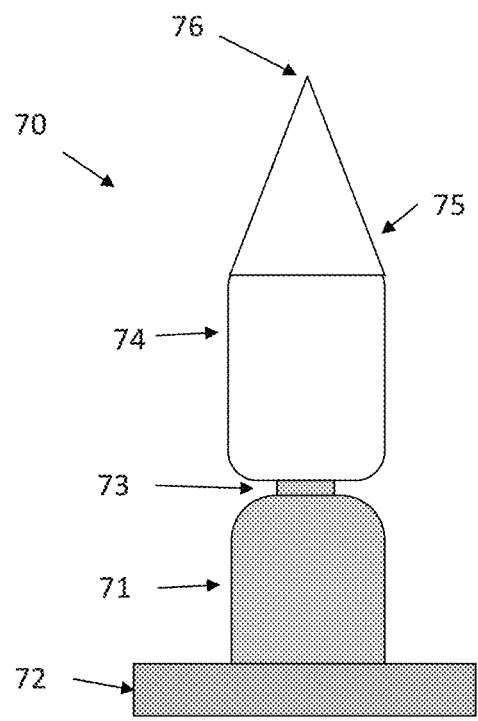
FIG. 7 is a schematic representation of an exemplary microneedle having a narrowed region to facilitate cleavage according to an embodiment of the disclosed subject matter.
Figure 8:
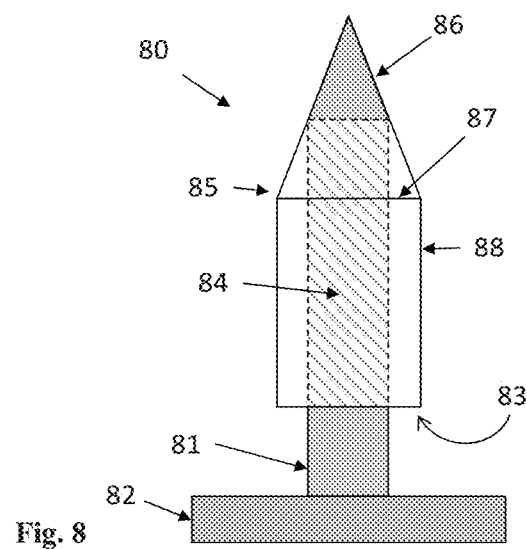
FIG. 8 is a schematic representation of an exemplary microneedle having a detachable coating on the outside of the microneedle shaft according to an embodiment of the disclosed subject matter.

Once in position proximate the RWM, the components of the device such as the driver and/or microneedle array can be advanced telescopically out of the introducer or catheter to operate to penetrate the RWM. An exemplary embodiment of the medical device is depicted schematically in FIG. 5 which illustrates the introducer or catheter inserted through the tympanic membrane to position a circular array of microneedles (shown enlarged) positioned proximate to the RWM. Other arrays are also contemplated, such as polygonal or oval.

The surgical instrument can be configured for pediatric indication or adult indication. For example, the length and diameter of the surgical instrument can be smaller for use for pediatric treatment.

In another aspect, the subject matter provides an apparatus including the microneedle or plurality of microneedles and driver formed as a unitary or non-separable device which can be disposable or reusable.

In another embodiment, the system or apparatus may further include an indicator to signal full penetration through the RWM. In this regard, the system or device may include a sensor to sense air, tissue, and/or fluid. Once the sensor senses fluid the sensor communicates with the indicator to signal full penetration through the RWM.

In yet another aspect, the system or apparatus may include an aspiration lumen and aspirator device. In this regard, the aspirator can aspirate fluid from the middle or inner ear, and deliver drugs locally to the middle or inner ear.

In an exemplary embodiment, the fabrication process of the microneedles is by isotropic etching combined with cryogenic processes that produce a taper. The fabrication parameters are enhanced and/or maximized to produce the designed shape.

Aspects of the disclosed subject matter include the following.

A microneedle comprising a longitudinal body having a detachable portion, wherein the detachable portion comprises therapeutic agent.

Embodiments of this aspect include the microneedle wherein the body has a maximum diameter less than about 20 microns; the microneedle wherein the body is hollow or solid; the microneedle wherein the body comprises silicon or tungsten; the microneedle wherein the body is configured with a taper along its length; the microneedle wherein the taper comprises a gradual taper having a gradual decrease in diameter along the length of the microneedle; the microneedle wherein the taper comprises a stepped taper with abrupt changes in diameter that serve as reinforcing ribs or ledges; the microneedle comprising a narrow region along the length of the body to facilitate cleavage of a portion of said body; the microneedle wherein the body includes proximal portion comprising a shaft and a distal end comprising a wide base and a narrow tip; the microneedle wherein the body comprises one or more projections or barbs that engage the distal side of the membrane after penetration through the membrane and is held in place thereby.

Another aspect of the disclosed subject matter includes an array comprising a plurality of any of the microneedles described above.

Another aspect of the disclosed subject matter includes a medical device comprising a plurality of any of the microneedles described above coupled to a base that is configured to physically engage a driver device capable of creating perforations in an anatomic barrier.

Embodiments of the medical device include those wherein the barrier is the round window membrane of an inner ear; wherein the medical device and the driver comprise separate components that are engaged to each other to define a modular system.

Another aspect of the disclosed subject matter is a system for delivering therapeutic agent to the inner ear of a subject which comprises an instrument for accessing the round window membrane; a plurality of microneedles of any of the embodiments described above, with sufficient rigidity to perforate the round window membrane.

Another aspect of the disclosed subject matter is a medical product for delivery of a therapeutic agent, comprising a microneedle configured to administer the therapeutic agent to the inner ear of a subject, wherein the needle includes a longitudinal body having a detachable portion, the detachable portion comprising therapeutic agent.

Embodiments of the medical product those wherein the microneedle longitudinal body has a maximum outer diameter less than about 100 microns along a portion of the body; wherein the microneedle longitudinal body has a maximum outer diameter less than about 50 microns along a portion of the body; wherein the microneedle longitudinal body has a maximum outer diameter less than about 20 microns along a portion of the body; wherein the microneedle longitudinal body has a maximum outer diameter less than about 1 micron along a portion of the body; wherein the microneedle body has a solid portion; wherein the microneedle body has a hollow portion; wherein the microneedle body comprises a biocompatible and biodegradable polymer or a biocompatible metal; wherein the microneedle body is configured with a taper along its length; wherein the taper comprises a gradual decrease in an outer diameter along a length of the microneedle longitudinal body; or wherein the taper comprises a stepped taper with abrupt changes to the outer diameter along a length of the microneedle longitudinal body; wherein the stepped taper provides one or more reinforcing ribs; wherein the microneedle comprises a narrow or pinched region along the length of the longitudinal body to facilitate cleavage of the detachable portion;

wherein the body includes a proximal portion comprising a shaft having an outer diameter and a distal portion having a polygonal shape.

Another aspect of the disclosed subject matter is an apparatus for penetrating a membrane, comprising:
- a plurality of needles including a first needle and a different second needle, the first needle including a first height and the second needle including a different second height, the first needle and the second needle being configured to (i) penetrate the membrane simultaneously to form a non-uniform design on the membrane, and (ii) penetrate the membrane at a uniform depth of insertion such that the depth of insertion of the first needle including the first height is the same as the depth of insertion of the second needle including the second height.

Embodiments of the apparatus include those wherein the first needle includes a lumen extending from a proximal portion to a distal end of the first needle, the lumen including a reservoir, the reservoir configured to carry a therapeutic agent; wherein the second needle includes a lumen extending from a proximal portion to a distal end of the second needle, the lumen including a reservoir for carrying a therapeutic agent; wherein the membrane includes at least one membrane of an inner ear or eye; wherein the first needle includes a distal tip coated with a biodegradable material; wherein the second needle includes a distal tip coated with a biodegradable material; wherein the distal end of the first needle is configured to move between an extended position and a retracted position based on difference in air pressure formed in the lumen; wherein the distal end of the first needle is configured to move between an extended position and a retracted position based on action of a piston inside the lumen; wherein the distal end of the second needle is configured to move between an extended position and a retracted position based on difference in air pressured formed in the lumen; and/or wherein the distal end of the second needle is configured to move between an extended position and a retracted position based on action of a piston inside the lumen.

Additional aspects and embodiments of the disclosed subject matter include the following.

A microneedle comprising a longitudinal body having a detachable portion, wherein the detachable portion comprises therapeutic agent.

Embodiments of the microneedle include a microneedle wherein the body has a maximum diameter from about 10 to about 150 microns; wherein the body is hollow or solid; wherein the body comprises silicon or tungsten; wherein the body is configured with a taper along at least a portion of its length; wherein the taper comprises a gradual taper having a gradual decrease in diameter along the length of the microneedle; wherein the taper comprises a stepped taper with abrupt changes in diameter that serve as reinforcing ribs or ledges; comprising a narrow region along the length of the body to facilitate cleavage of a portion of said body; wherein the body includes proximal portion comprising a shaft and a distal end comprising a wide base and a narrow tip; wherein the body comprises one or more projections or barbs that engage the distal side of the membrane after penetration through the membrane and is held in place thereby; wherein the microneedle body comprises a biocompatible and biodegradable polymer or a biocompatible metal; or any combination of the foregoing.

Another aspect is an array comprising one or a plurality of the microneedles described above.

Another aspect is a medical device comprising one or a plurality of microneedles described above coupled to a base that is configured to physically engage a driver device capable of creating perforations in an anatomic barrier.

Embodiments of the medical device include those wherein the barrier is the round window membrane of an inner ear; wherein the medical device and the driver comprise separate components that are engaged to each other to define a modular system.

Another aspect is a system for delivering therapeutic agent to the inner ear of a subject which comprises an instrument for accessing the round window membrane; a plurality of microneedles as described above, with sufficient rigidity to perforate the round window membrane; and a driver, wherein the plurality of microneedles is coupled to the driver.

Another aspect is a medical product for delivery of a therapeutic agent, comprising a microneedle according to any of the embodiments above configured to administer the therapeutic agent to the inner ear of a subject, wherein the needle includes a longitudinal body having a detachable portion, the detachable portion comprising therapeutic agent.

Another aspect is an apparatus for penetrating a membrane, comprising:
- a plurality of microneedles including a first microneedle of any of the embodiments above and a second microneedle of any of the embodiments above, wherein the first needle and the second needle are different.

Embodiments of this aspect include the apparatus wherein the first needle comprises a first height and the second needle comprises a different second height, the first needle and the second needle being configured to (i) penetrate the membrane simultaneously to form a non-uniform design on the membrane, and (ii) penetrate the membrane at a uniform depth of insertion such that the depth of insertion of the first needle including the first height is the same as the depth of insertion of the second needle including the second height; such as wherein the first needle includes a lumen extending from a proximal portion to a distal end of the first needle, the lumen including a reservoir, the reservoir configured to carry a therapeutic agent; or wherein the second needle includes a lumen extending from a proximal portion to a distal end of the second needle, the lumen including a reservoir for carrying a therapeutic agent; wherein the membrane includes at least one membrane of an inner ear or eye; wherein the first needle includes a distal tip coated with a biodegradable material; wherein the second needle includes a distal tip coated with a biodegradable material; wherein the distal end of the first needle is configured to move between an extended position and a retracted position based on difference in air pressure formed in the lumen; wherein the distal end of the first needle is configured to move between an extended position and a retracted position based on action of a piston inside the lumen; wherein the distal end of the second needle is configured to move between an extended position and a retracted position based on difference in air pressured formed in the lumen; wherein the distal end of the second needle is configured to move between an extended position and a retracted position based on action of a piston inside the lumen; the apparatus configured to selectively retract the first microneedle or a first portion of the plurality of microneedles from the membrane while the second microneedle or a second portion of the plurality of microneedles remains penetrated into the membrane, thereby exposing microperforation(s) formed by the first needle or the first portion of the plurality of the microneedles for delivery of a therapeutic agent through the membrane; and/or wherein the first microneedle or a first portion of a plurality of microneedles is configured with barbed tip(s) to securely engage the membrane and hold the apparatus in place while the second microneedle or a second portion of the plurality of microneedles is configured to deliver a therapeutic agent through the membrane.

Another aspect is a method for preparing a microneedle or a microneedle array comprising one or a plurality of microneedles on a base, the method comprising designing a microneedle configured to penetrate a membrane with a rupture force of from 0.4 to 5 milliNewtons;

configuring a two-photon polymerization lithography apparatus to fabricate the microneedle or microneedle array on a base according to the design; and operating the two-photon polymerization lithography apparatus to prepare the microneedle or microneedle array.

Embodiments of this aspect include the method used to prepare the microneedle of any of the embodiments above; and/or wherein the membrane to be penetrated by the prepared microneedle is a round window membrane.

Polymeric materials are receiving some interest from the medical industry because of their ease of manufacture, low cost and favorable biological and mechanical properties.

A simple and versatile fabrication process directly linking three-dimensional (3D) modeling and simulation with microscale printing and replication is described herein. The process involves microstructures fabricated by 3D stereolithography directly from CAD drawings, which are then replicated by soft embossing.

Alternatively or additionally, the microneedles or portions thereof may be formed of metals, including for example, copper, tungsten, platinum, palladium, alloys such as steel (iron alloyed with various other metals), CoCr alloys, CoCrMo alloys, TiAlV alloys and WE43 magnesium alloys, or materials including titanium nitride, titanium carbon nitride, titanium aluminum nitride, aluminum titanium nitride, and zirconium nitride. For example, metals may be electrodeposited onto polymeric substrates to provide solid or hollow microneedles comprising metal and polymer components. Metal components of the microneedles may provide stronger, more durable and/or sharper microneedles than solely polymeric needles. Alternatively, a polymeric mold or substrate may be electrodeposited with metal, followed by destruction of the polymeric substrate to produce a metal microneedle. Notably, the polymeric substrates may be prepared by two-photon polymerization as described herein.

In some embodiments, the microneedle may comprise a proximal portion, as described above, comprising metal, and a distal, cleavable portion comprising a polymer and/or a therapeutic agent. For example, a microneedle comprising a proximal metal portion may be coated with a biodegradable polymer and/or therapeutic agent as described for FIG. 8. Alternatively, a microneedle comprising a proximal metal portion and a lumen may be combined with a biodegradable polymer and/or therapeutic agent as described for FIGS. 4, 9A and 9B.

Figure 20:
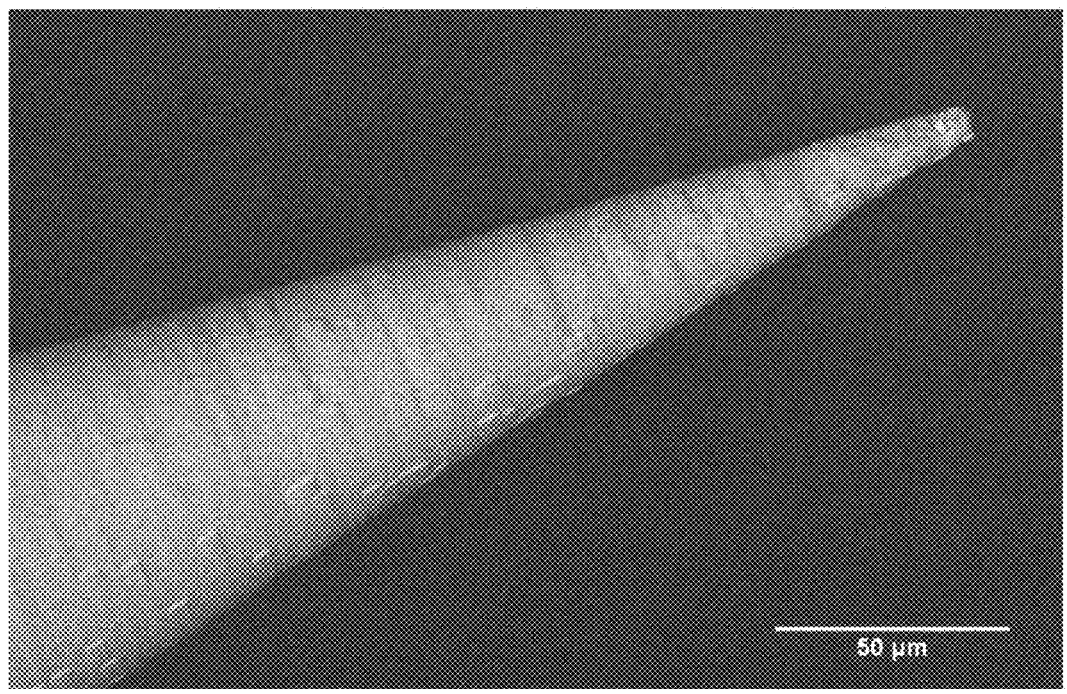
FIG. 20 shows a micrograph of a needle tip of an exemplary microneedle blunted after penetration of a round window membrane.
Figure 21:
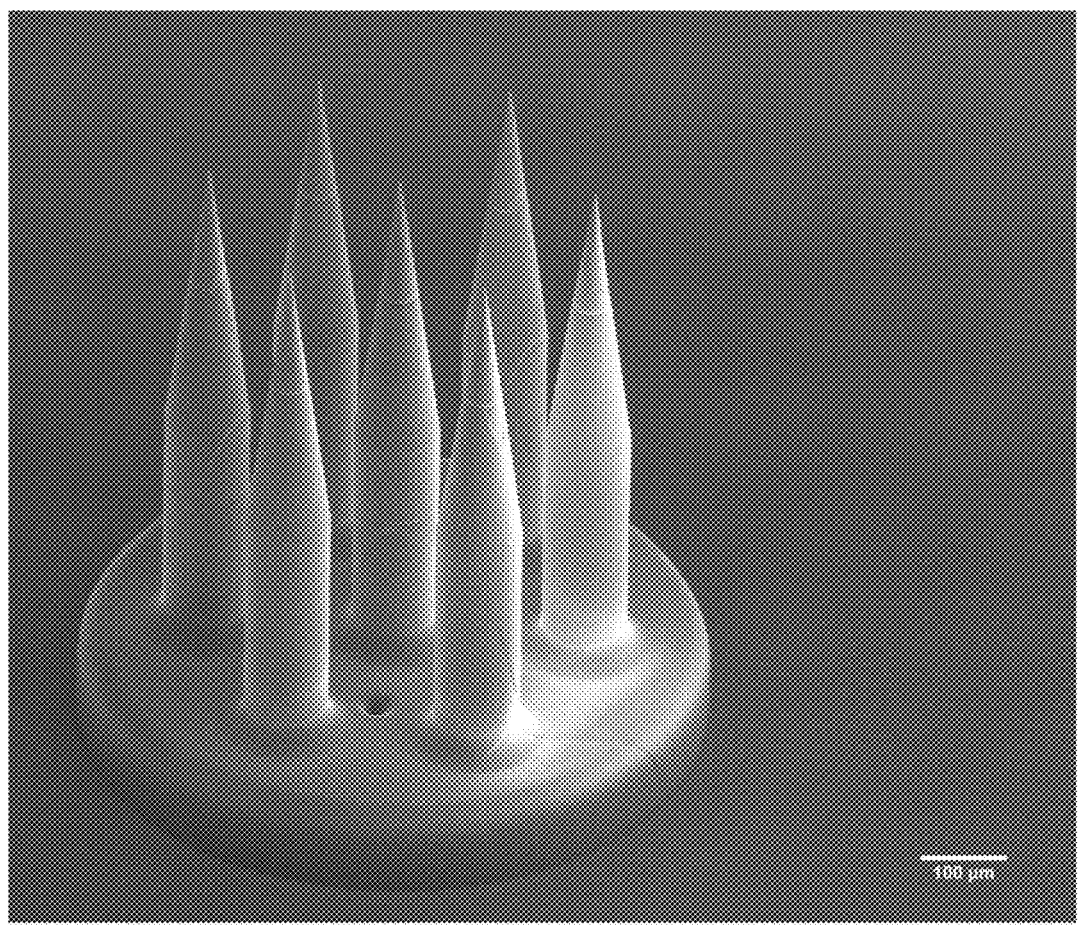
FIG. 21 shows a micrograph of an exemplary microneedle array design having seven microneedles prepared by two-photon polymerization according to an embodiment of the disclosed subject matter.

Alternatively, a polymeric microneedle may be coated with a metal or nitride coating to provide a harder, stronger, less deformable tip than that of a solely polymeric microneedle, as discussed in relation to FIG. 20.

Fabrication of Master Microneedles

Polymeric master microneedles may be fabricated by 3D laser lithography using the Photonic Professional GT system (Nanoscribe GmbH, Karlsruhe, Germany). The direct laser writing (DLW) technique, also known as two-photon polymerization (TPP) or 3D laser lithography, is a nonlinear optical process based on two-photon absorption (TPA) theory. The Nanoscribe system is equipped with a pulsed erbium-doped femtosecond (frequency-doubled) fiber laser source with a center wavelength of 780 nm for the exposure of the photoresist. At the pulse length of 100-200 femtosecond the laser power ranges between 50-150 mW. For fabrication of microneedles CAD models may be generated by SolidWorks software (Dassault Systems SolidWorks Corporation, Concord, NH, USA) in stereolithography (STL) file format and imported to the software package Describe (Nanoscribe GmbH, Germany) for scripting of writing parameters. The laser beam is focused into the negative-tone photoresist, IP-S (Nanoscribe GmbH, Karlsruhe, Germany), using a Dip-in laser lithography (DiLL) objective with ×25 magnifications and NA=0.8.

In this process, the objective lens is directly dipped into the liquid and uncured photoresist acts as both photosensitive and immersion medium in an inverted fabrication manner. The refractive index of the photoresist defines the focal intensity distribution. For the DiLL process the objective working distance does not limit the height of the sample; therefore, structures with micrometer to millimeter heights can be fabricated. A drop of resist is cast on the silicon substrate; IP-S exhibits good adhesion on the silicon substrate, and is loaded onto the system. Microneedle arrays are written in galvo scan mode (XY) and piezo Z offsetting mode. The arrays may be split into blocks of about 200-400 μm×200-400 μm×10-250 μm (XYZ), within the working range of the galvo scan mode. Blocks can be stitched together to create larger arrays. Depending on the design, the laser power can be 50-150 mW, with scan speed of 5-10 cm $s^{-1}$, with minimum and maximum slicing distance 0.1 and 0.5 μm. After exposure, the structures are developed in propylene glycol monomethyl ether acetate (PGMEA) bath for 10-60 minutes plus two 20-30 minute isopropyl alcohol (IPA) rinses followed by 20 min flood exposure through a UV light source with 16 mW $cm^{-2}$ intensity to further crosslink the photosensitive material.

Casting of Negative Elastomeric Mold

A 'soft' negative impression of the masters may be cast using silicone elastomer polydimethylsiloxane (PDMS) (SYLGARD 184 Silicone Elastomer Kit, Dow Corning, Midland, MI, USA) with a base/curing agent ratio of 10:1 in a Petri dish. The mixture may be degassed in a vacuum chamber for 60 min to suppress formation of air bubbles during the subsequent curing stage in a standard laboratory oven at 60° C. overnight. The cured PDMS molds are peeled off the master prototypes to be used as negative molds for microneedles replication.

Embossing Thermoplastic Materials Using Negative Elastomeric Molds

Thermoplastic microneedle replicas are prepared by a soft embossing process, which may be performed on a rheometer (such as Kinexus Rheometer, Malvern Instruments Ltd., Worcestershire, UK) using the PDMS-negative molds. 'Soft' negative impressions of the master prototype microneedles are cast using the silicone elastomer, PDMS. One or two thermoplastic pellets (cyclo-olefin polymer, Zeonor 1060R) are loaded onto each cavity of the PDMS negative molds and placed between two 20 mm diameter stainless steel plates. The upper plate is lowered until the plates are in contact and heated up to 160° C., 60° C. above the glass transition temperature of the thermoplastic (Tg=100° C.). This molding temperature decreases the viscosity of the molten thermoplastic so that it easily penetrates the negative mold cavities. The upper plate is then lowered further as the thermoplastic melts, until a specified target force is reached. A maximum force of 15-25 N may be applied during this embossing process. In order to achieve consistent and uniform embossing, the molding temperature may be fixed at 160° C. for around 15 min throughout the embossing process, while the desired gap between the plates is achieved by applying a calibrated force. Then the mold and molten polymer are cooled down to 10-15° C. for 10-15 min with constant force (such as 1.6 N) before demolding. The solidified thermoplastic microneedle arrays are separated from the PDMS elastomeric mold without fracture or defect. The molds may be used many times (for example, at least 20 cycles).

Oxygen Plasma Treatment

In order to facilitate filling of microneedle channels and reservoirs by capillary pressure, the hydrophobic thermoplastic can be surface treated to reduce its contact angle to below 90°. Oxygen plasma treatment increases the free energy of the surface by creating hydrophilic, oxygen-containing groups such as carbonyl and carboxyl esters on the surface. Oxygen plasma treatment may be performed on the thermoplastic microneedle arrays using an oxygen plasma etcher (PE-250 Plasma etcher, Denton vacuum, USA) with 50 W RF power and 340 mTorr pressure for 20 min.

EXAMPLES

Microneedle Fabrication

We employed single crystal Si (100) wafers as the substrate material for 2PP laser writing due to its low price and commercially-available highly polished surface. The Si wafers were cut into 25×25 mm square slides followed by Piranha cleaning and rinsing with acetone and isopropyl alcohol (IPA) to ensure a clean surface.

The 2PP 3D laser writing was performed using the Photonic Professional GT system (Nanoscribe GmbH, Karlsruhe, Germany). The photoresist employed was IP-S (Nanoscribe GmbH, Karlsruhe, Germany) in a Dip-in Laser Lithography (DiLL) configuration with a 25× objective (Nanoscribe GmbH, Karlsruhe, Germany). Stereolithography (STL) files were generated using the SolidWorks (Dassault Systems SolidWorks Corporation, Concord, NH, USA) computer aided design (CAD) soft-ware. These subsequently were converted into Direct Laser Writing commands via the Describe (Nanoscribe GmbH, Karlsruhe, Germany) software.

The proprietary IP-S photoresist was drop cast onto the substrate, and the microscope objective was immersed into the photoresist. The 2PP writing started at the out-of-plane z-position of 1 μm within the substrate to ensure good anchoring as well as to account for possible slight tilting of the substrate. Other writing parameters such as writing speed (40000 μm/s), laser intensity (35% at interface, 100% at scaffolds and 100% at contours), hatching distance (0.75 μm) were also specified after multiple trials. The stage was mobilized using the piezo-motor and the laser was used to scan the field of view of the objective using galvo-scan mode. Since the field of vision of the laser is not wide enough to write the entire structure, the structure to be written was divided into hexagonal regions with the major axis set at 350 μm, and the stage was used to move between these regions and write them separately, leaving an overlap of 2 μm for good stitching.

After 2PP writing was complete, the samples were put into a propylene glycol monomethyl ether acetate (PGMEA) solution for 20 minutes, and were subsequently cleaned in two IPA baths of length 35 minutes and 25 minutes. The extended IPA baths were necessary to remove uncured photoresist from an annular cavity in the base of the needle, which will be discussed in the next section. Nanoscribe GmbH (Karlsruhe, Germany) [25] reports that the resulting polymer has mechanical properties with approximate values: Young's modulus of 4.5 GPa, hardness of 160 MPa, storage modulus of 5 GPa, and loss modulus of 150-350 MPa. All data were acquired with a G200 Nanoindenter. The specimen from which Young's modulus and hardness were measured was a 100×100×100 $\mu m^3$ solid block written with the 25×0.8 objective using the following parameters: slicing: 1 μm; hatching 0.5 μm. The specimen from which storage and loss moduli were acquired was cylindrical with a 10 μm diameter at a temperature of 26° C.

Microneedle Design and Fabrication

We designed and fabricate microneedles to perforate the RWM of a guinea pig (GP), which has a thickness of approximately 10-30 μm. FIGS. 2A and 2B show the final microneedle design. For simplicity we designed a solid cylindrical needle with a constant shank radius of 50 μm and height 200 μm with a subsequent 9° taper to the needle tip. The very small voxel size attainable with 2PP printing allows ultra-sharp needles to be printed. Here we define the "sharpness" of a needle as the radius of curvature of its tip. In order to perforate a membrane efficiently, the radius of curvature of the microneedle tip must be much less than the thickness of the membrane. In this study, we specified the needle radius of curvature to be 500 nm. FIG. 2A shows a center cross-section of the microneedle with associated base.

The base of the needle was designed with practicality in mind. One shortcoming of structures made using microfabrication methods is the difficulty of readily mounting them to tools easily utilizable by clinicians. In the present study, this challenge was overcome by designing the base of the microneedle structure to be mounted directly onto a commercially available Gauge 23 syringe tip (industrial unsterilized Blunt Tip Dispensing Needle with Luer Lock) of length 12.7 mm, inside radius of 170 μm and outside radius of 320 μm. An annular cavity in the base serves to mate the base to the blunt dispensing needle. To reduce printing time, the base of the needle was designed to be partially hollow. In order to allow a pathway for the uncured IP-S photoresist within the base to exit, small holes or channels were incorporated into the interior surface of the annular cavity. A 3D rendering of the design is shown in FIG. 2B.

Figure 10A:
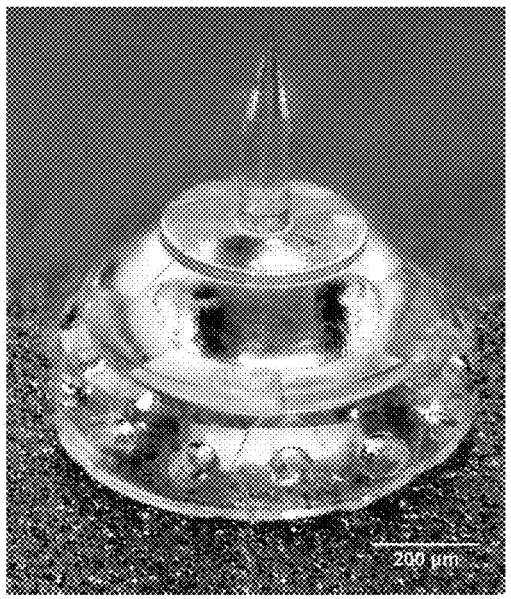
FIGS. 10A-10D show micrographs of an exemplary microneedle array according to the design of FIG. 1A prepared by two-photon polymerization.
Figure 10B:
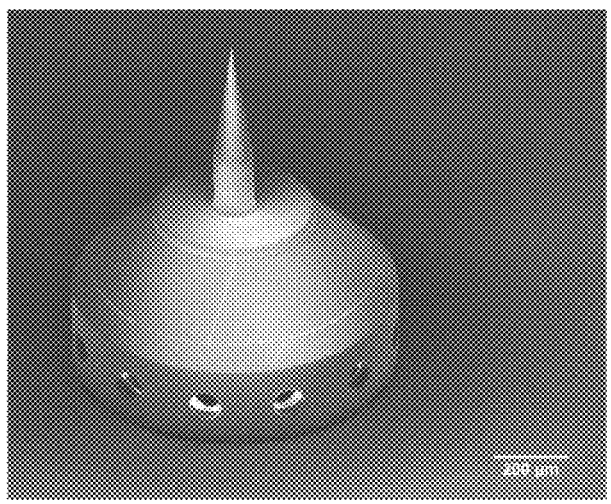
Figure 10C:
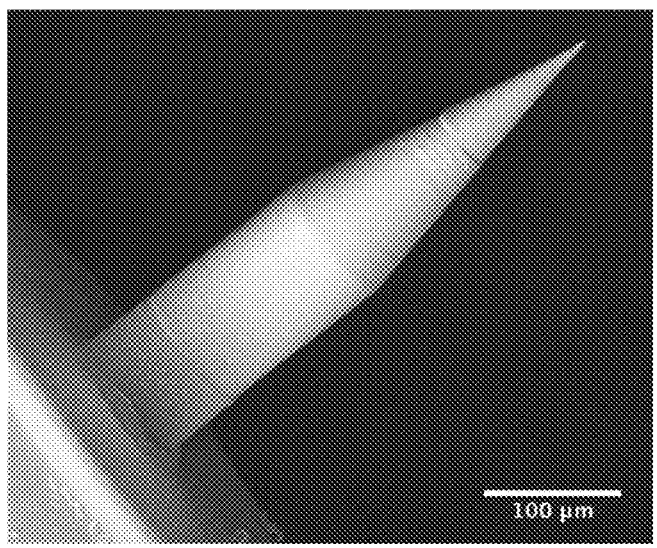
Figure 10D:
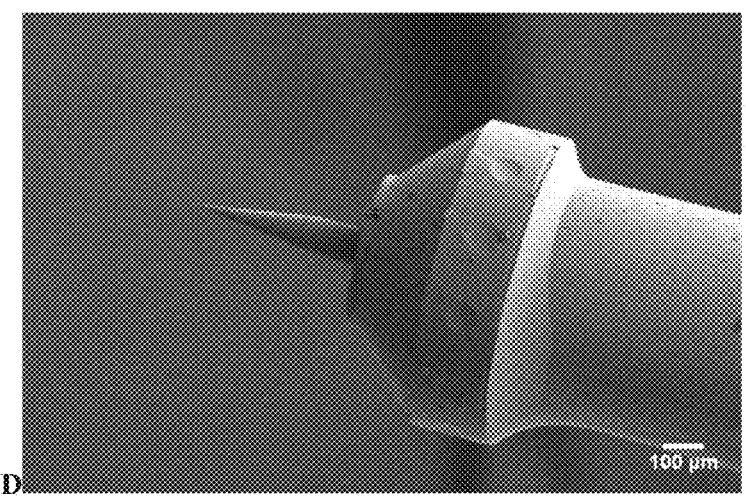
Figure 11:
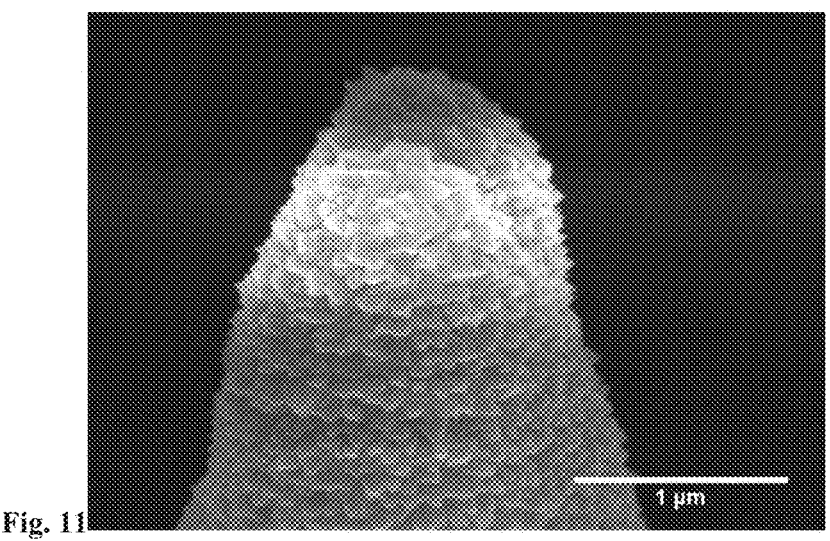
FIG. 11 shows a micrograph of a needle tip of an exemplary microneedle array according to an embodiment of the disclosed subject matter.

FIGS. 10A to 10D show images of the printed microneedles. FIG. 10A is an optical image of the microneedle and base sitting atop a reflective substrate, which accounts for the apparently extra array of holes distributed circumferentially around the base. FIG. 10B shows a SEM (Zeiss, Oberkochen, Germany) micrograph of a printed microneedle and its base. FIG. 10C shows a SEM (Zeiss, Oberkochen, Germany) micrograph of a printed microneedle. FIG. 10D shows the microneedle and base mounted on a Gauge 23 blunt syringe tip and secured by resin epoxy. Finally, FIG. 11 shows a high-magnification SEM micrograph of the microneedle tip coated with sputtered titanium, for characterizing tip geometry. The surface roughness has a length scale of about 100 nm, which coincides with the precision easily obtainable in 2PP lithography processes. The image confirms the tip radius to be 500 nm or smaller. The sizes of the individual voxels—apparent in this image—are much smaller than the wavelengths of visible light, so the microneedle surface is specularly reflective at visible wavelengths.

Harvesting Guinea Pig Cochleae

Carcasses of mature guinea pigs (Hartley, Charles River, Massachusetts) with no history of middle ear disease were obtained via tissue sharing facilitated by the Institute of Comparative Medicine at Columbia University Medical Center. All animals were euthanized using pentobarbital overdose for the purpose of harvesting their trachea. Immediately following euthanasia, the intact temporal bone of the guinea pig was harvested using blunt dissection. An Osada Electric Handpiece System (Osada, Inc., Los Angeles, California, USA) was used to drill and remove the surrounding bone, exposing a clear, wide-angle view of the RWM. The resulting specimen was rinsed with 0.9% saline solution and inspected for gross membrane perforations and fractures of the RWM niche. If perforation of the RWM with the microneedles could not be performed immediately, the specimen was refrigerated in 0.9% saline solution (up to a maximum of 24 hours) prior to further experimental use. During perforation experiments, small amounts of sterile 0.9% saline solution were applied at regular intervals to keep the membrane from drying.

Instrumented Indentation of Cochlea with Microneedle

A microindenter setup was built in-house for repeatable controlled perforations of the harvested RWM. The system measures the force vs. displacement response during indentation. It consists of the following components:

Motorized stage for moving harvested RWM into position (Zaber Technologies Inc., Vancouver, British Columbia, Canada)

Motorized linear translator onto which the indenter needle is mounted (Zaber Technologies Inc., Vancouver, British Columbia, Canada)

Force transducer with full scale of 10 grams-force for measurement of axial force exerted on needle during indentation (Transducer Techniques, Temecula, California, USA).

Figure 12:
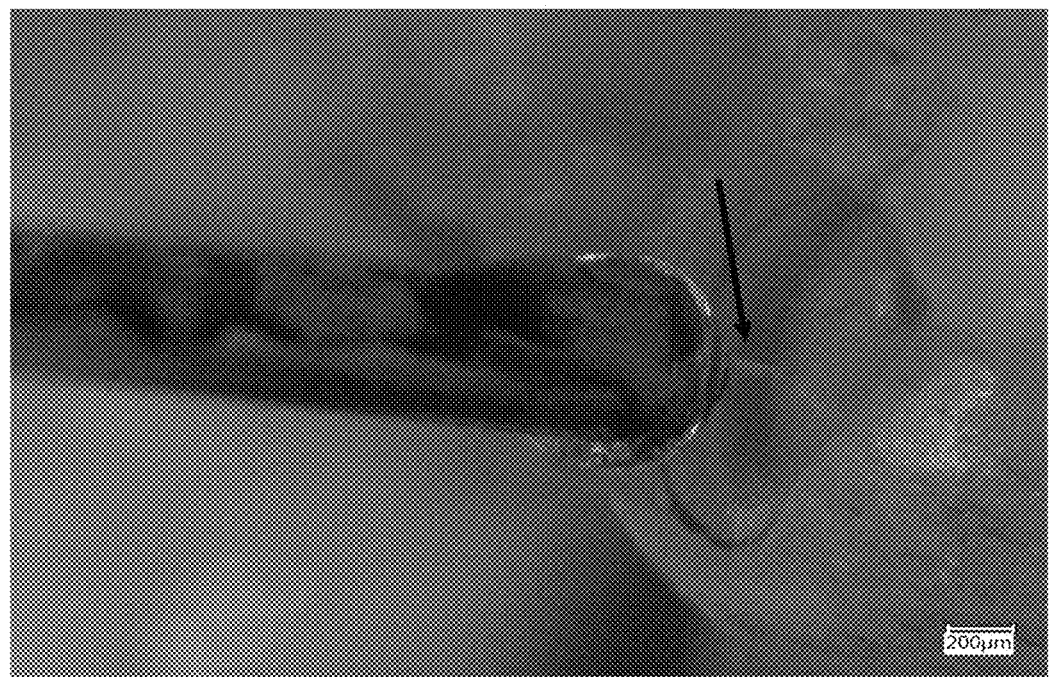
FIG. 12 shows a micrographic image of an exemplary microneedle during an indentation and perforation of a guinea pig round window membrane according to an embodiment of the disclosed subject matter.

The indentation experiment was conducted with a constant needle speed of 5 µm/s. Imaging during in vitro experimentation was made using a 3D digital microscope (VHX-5000, Keyence Corporation of America, Elmwood Park, NJ, USA). The images and videos acquired via the digital microscope were used to position the RWM in relation to the microneedle, as well as to verify positions of perforations, in conjunction with the force data acquired during perforation. FIG. 12 shows an image of the microneedle (indicated by the arrow) during the indentation and perforation process of the RWM.

Confocal Microscopy of Perforated Membranes

After perforation and prior to imaging, the RWM was immersed in a 1 mM solution of Rhodamine B in phosphate buffered saline (PBS) for 1 hour. It was then rinsed several times with PBS and placed in a MatTek glass bottom dish (No. 1.5). The imaging of the perforated membrane was done on an inverted confocal laser scanning microscope Zeiss LSM 880, Axio Observer with a 10× objective (EC Plan-Neofluar 10×/0.30 M27) or a 20× objective (Plan-Apochromat 20×/0.8 M27). An excitation wavelength of 561 nm was chosen for the laser, and emitted light from 576 nm to 682 nm was allowed to pass to the detector. A stack of images was generated at several focal heights spaced 1 µm and 5 µm apart for the 20× objective and the 10× objective, respectively. These images were then projected in the stacking direction (maximum intensity z-projection) to obtain a global image with the visible perforation.

Results

Perforation Force Data

Figure 13:
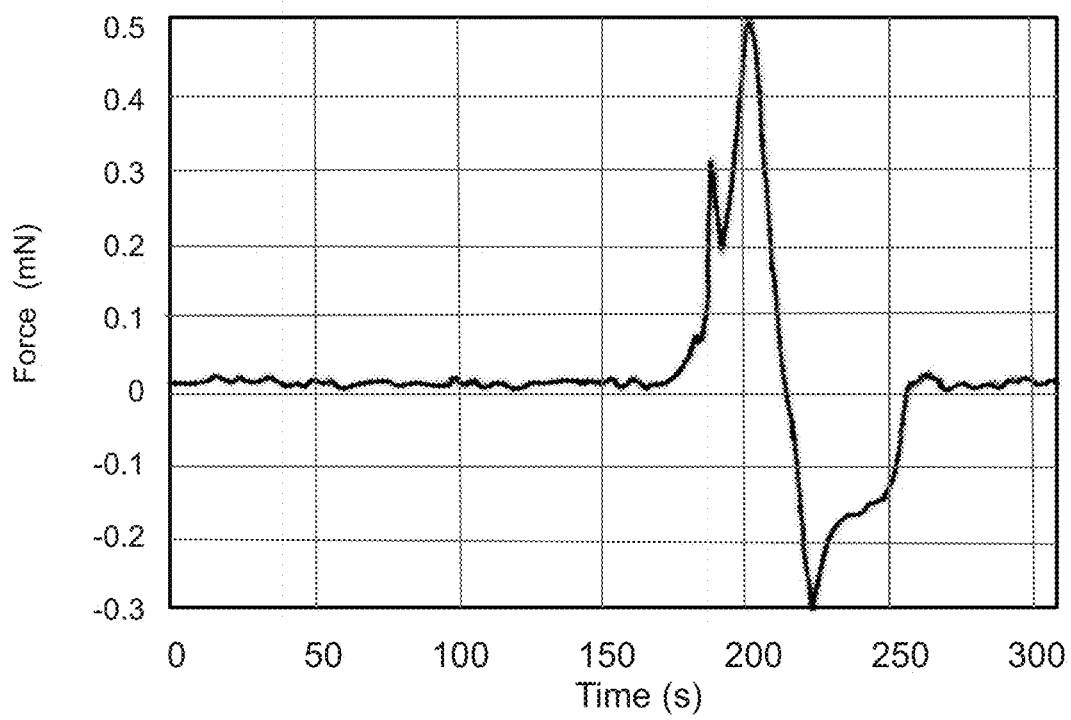
FIG. 13 shows a plot of the force vs. time of an indentation and perforation of a guinea pig round window membrane with the exemplary microneedle according to an embodiment of the disclosed subject matter.

We first consider the force on the microneedle necessary to perforate the RWM at a constant velocity, in this case 5 µm/s. A representative plot of force vs. time in FIG. 13 shows a local maximum and a global maximum in force. Contact of the microneedle tip with the RWM occurs around t=175 s. The recorded indentation force is 0.29 mN, when t=190 s, at which time the needle tip initially perforates the RWM. The force then increases again as the tapered portion of the needle enlarges the perforation with further displacement through the RWM. The entirety of the tapered section of the needle passes through the membrane after t=200 s, and is retracted upon visual confirmation of the event. The force necessary for further perforation decreases because the perforation has reached its maximum size. As the needle travels back, from t=215 s to t=260 s, a negative force is seen to act on the needle. This is due to the friction between the membrane and the needle.

We interpret the initial local maximum to be the force at which the microneedle tip "pops" through the RWM to make an initial perforation. The size of this initial perforation scales with the microneedle tip radius rather than the shank radius. Therefore, the microneedle must enlarge the perforation by continuing to move through the RWM until the shank fully perforates it, which occurs at the global maximum in force. In all cases, we report the global maximum as the "Perforation Force." The details of the initial perforation event likely depends upon tip radius as well as the angle of the taper.

The local maximum force at initiation of the perforation is important for the detailed design of the needle tip. The force vs. time plot for some of the perforations did not exhibit the initial local maximum, which may indicate that the microneedle tip does not "pop" through the RWM. In this case we expect the perforation process to be continuous. The global maximum depends upon the microneedle shank radius and to a lesser extent on the velocity of penetration as a consequence of viscoelastic behavior in the RWM. The value of this global maximum is an important design consideration for the overall size and shape of the microneedle.

Figure 14:
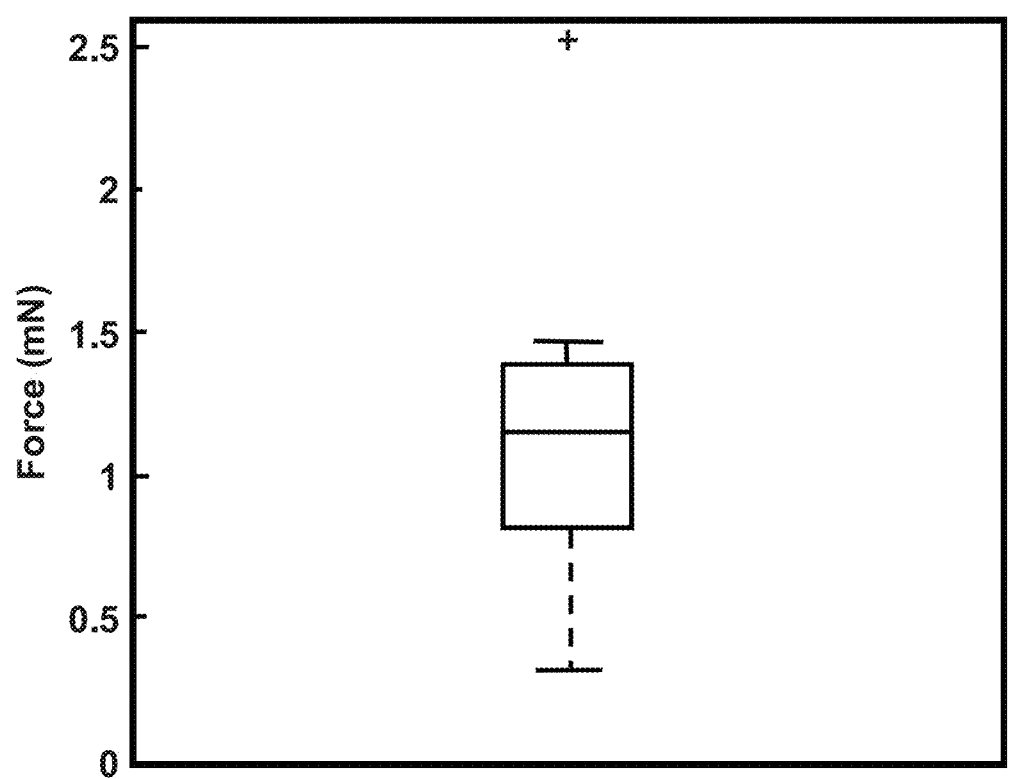
FIG. 14 shows a statistical plot of the force observed for several indentation and perforations of a guinea pig round window membrane with the exemplary microneedle according to an embodiment of the disclosed subject matter.

FIG. 14 shows the distribution of the perforation force data, as a box plot for measured perforation forces. The bottom and top edges of the box indicate the 25th and 75th percentiles, respectively. The mean value is halfway between the 25th and 75th percentiles. The horizontal central mark indicates the median. The vertical whiskers extend to the most extreme data points not considered outliers, and outliers are plotted individually using the symbol. The results show a mean perforation force of 1.19 mN and a standard deviation of 0.61 mN. With our data of n=9, we have executed a single tailed t-test and observed with a 95% confidence level that the mean perforation force for the manufactured needles is less than 1.6 mN, for Guinea Pig Round Window Membranes with the produced microneedles.

Analysis of Perforations with Confocal Microscopy

Figure 15:
FIGS. 15, 16 and 17 show micrographs of perforations of a round window membrane by an exemplary microneedle according to an embodiment of the disclosed subject matter.

The shape and area of the perforations created with the microneedles were studied by imaging the RWM with a confocal microscope. FIG. 15 shows a confocal image of an entire Round Window Membrane in approximate plan view with a perforation roughly in its center made by a microneedle with a 50 µm radius manufactured using 2PP. The perforation is lens-shaped and remained partially open after the microneedle was removed. The non-circular shape of the perforation indicates anisotropy of the microstructure and mechanical properties of the RWM, consistent with our previous studies with a non-circular microneedle.

Figure 16:
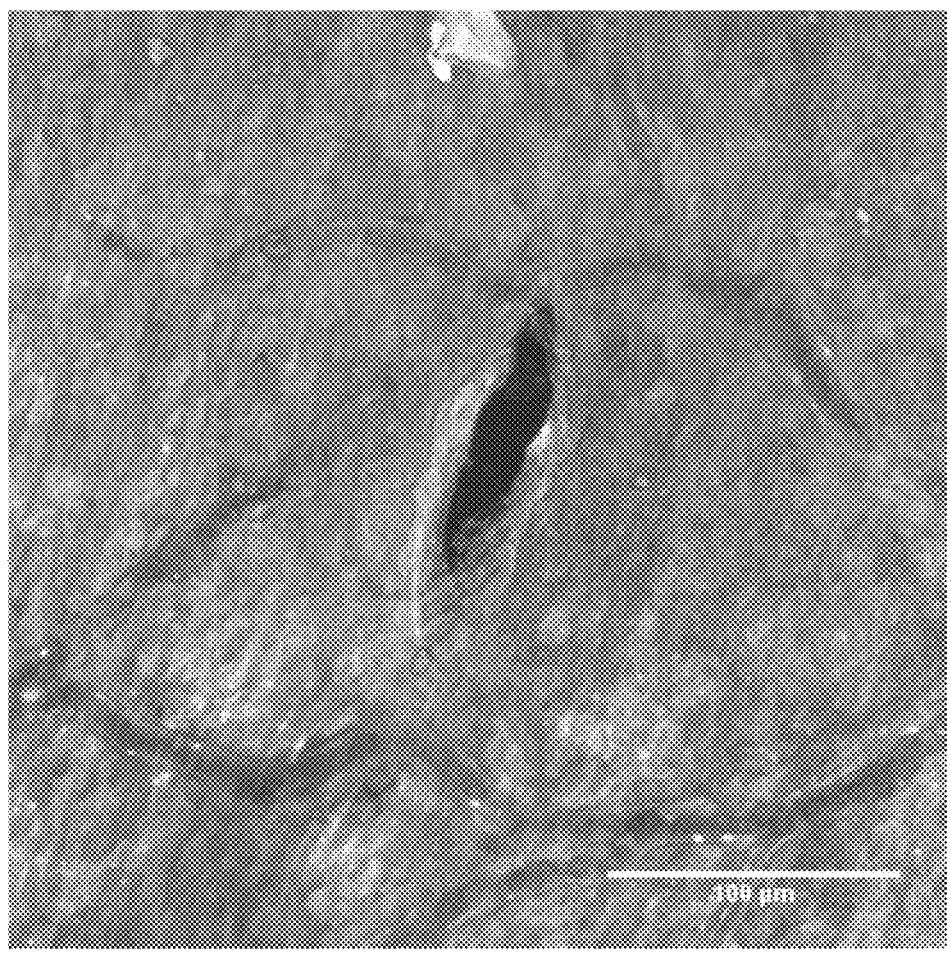

FIG. 16 shows a higher magnification confocal image of the membrane in the region that contains the perforation. Blood vessels containing red blood cells with blood vessels can be seen for size comparison. Guinea pigs have red blood cells that are around 7.4 µm in diameter. The length of the residual opening in the major axis has a mean of 95.9 µm and a standard deviation of 7.8 µm, which is essentially the same as the microneedle diameter of 100 µm. However, the length of the residual opening in the minor axis is only about 25% of the microneedle diameter: the measurements have a mean of 25.4 µm with a standard deviation of 6.3 µm.

Figure 17:
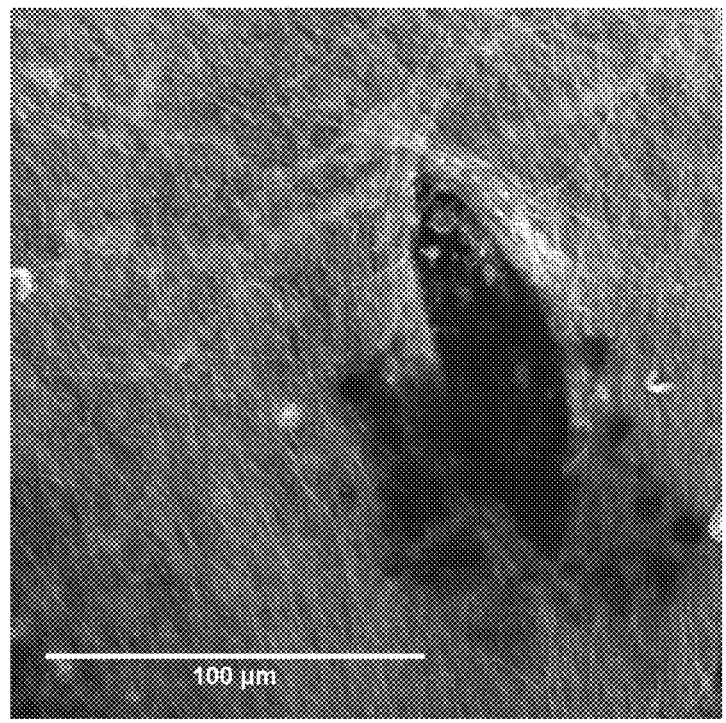

FIG. 17 shows a confocal microscopy image at a higher magnification that resolves the various fibers of the connective tissue within the RWM tissue. The direction of the major axis of the lens-shaped perforation is roughly aligned with the main direction of the fibers of connective tissue. Fiber reorientation at the crack tip can be observed. The small dark circular features are cellular debris occluding the view. The images in FIGS. 16 and 17 demonstrate that the perforation shape is dependent on the structure of the membrane in addition to the diameter of the microneedle.

Figure 18:
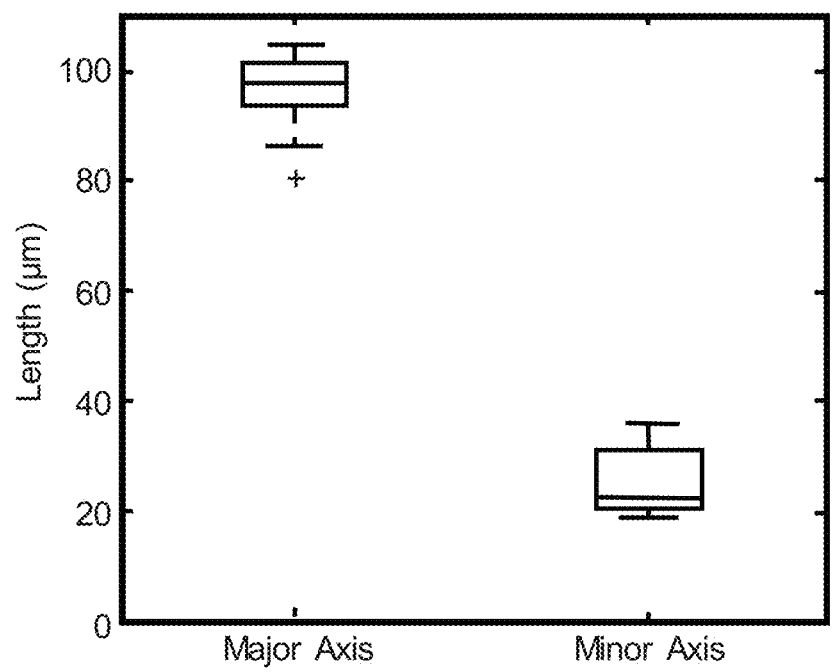
FIG. 18 shows statistical plots of the major and minor axes of microperforations of a guinea pig round window membrane made with an exemplary microneedle according to an embodiment of the disclosed subject matter.
Figure 19:
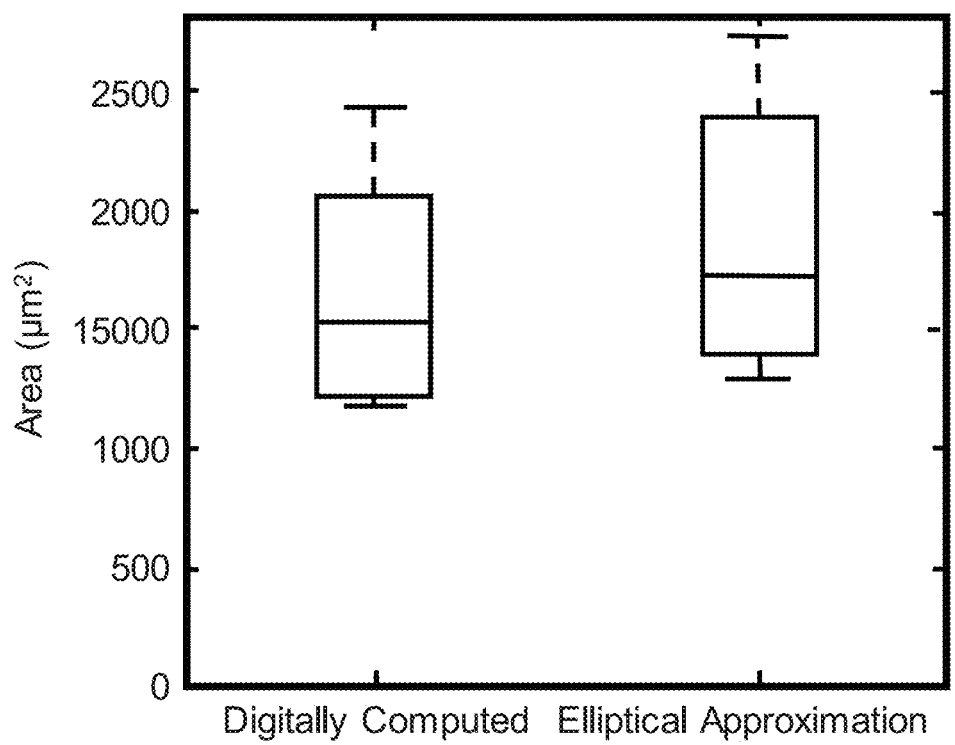
FIG. 19 shows statistical plots of the major and minor axes of several microperforations of a guinea pig round window membrane made with an exemplary microneedle according to an embodiment of the disclosed subject matter.

FIG. 18 shows box plots quantifying the lengths of the major and minor axes and FIG. 19 shows box plots quantifying the open perforated area. The bottom and top edges of the boxes indicate the 25th and 75th percentiles, respectively. The mean value of each plot is halfway between the 25th and 75th percentiles. The horizontal central mark indicates the median. The vertical whiskers extend to the most extreme data points not considered outliers, and outliers are plotted individually using the '+' symbol. When the microneedle is inserted fully into the RWM, both the major and minor axes of the perforation must be at least the same as the shank diameter. Upon retraction of the needle the opening in the direction of the minor axis decreases to about 25% of that length while the opening of the major axis does not decrease significantly if at all.

The resulting area of the holes were observed to have a mean and standard deviation of 1670 µm$^2$ and 476 µm$^2$, respectively. This area was computed digitally, and it was of interest to determine if the resulting area was similar to that of an ellipse with the identical major and minor axes. FIG. 19 illustrates this comparison, and it is clear that estimating the area from the major and minor axes alone is not viable solution. A paired t-test shows that the elliptical approximation—due to the nature of the shape of the edges of our perforations—does overestimate the actual area with a significance level of 95%.

The long term goal of the research described herein is to demonstrate that microperforations in the RWM can enhance the accuracy and precision of therapeutic transport into the cochlea via intratympanic injection into the middle ear space followed by diffusion across the RWM into the cochlea. In this paper we focus on a novel fabrication method of microneedles used to perforate the RWM and report on the force necessary for perforation as well as the size and shape of the resulting perforations. The shape and area of perforations are of interest because they will play a significant role in determining the rate at which therapeutics diffuse across a perforated RWM. In this section we discuss the implications of our results on design of the needles.

The RWM is in a state of tensile prestress prior to perforation. As a consequence, there exists a critical threshold size of perforation below which a stable perforation can be introduced and above which the perforation will propagate unstably into a tear or rip. We do not know the critical size because the magnitude of the prestress has not been quantified. However clearly the critical size exceeds 100 µm in guinea pig RWMs because we have successfully introduced stable perforations of that size.

The size of a RWM perforation is determined by the size of the microneedle shank. Small RWM perforations are desirable for several reasons. First, while our goal is to introduce therapeutics into the cochlea, we must do so while minimizing leakage of perilymph from the scala tympani chamber of the cochlea into the middle ear space. An outward perilymph flux will transport therapeutic material from the inner ear, preventing the medication from acting upon the cochlea. Microperforations impose a higher viscous resistance to fluid flow compared to larger perforations. As a consequence, the microperforations allow for the diffusive transport of therapeutic reagents into the cochlea while minimizing fluid flux out of the cochlea. Second, when the perforation in the RWM is smaller, the perforation will remain patent for a shorter amount of time before healing, and it will undergo a less prominent change in its structure. Third, a small perforation reduces the probability of transmission of infection into the cochlea due to treatment.

Needle sharpness (i.e. needle tip radius of curvature) is a crucial design and fabrication parameter to ensure safe perforation of the RWM. As needle sharpness increases, the force required for perforation decreases and the risk of trauma to the RWM reduces. Excessive application of force during surgical manipulation of the RWM risks detachment of the RWM from its sulcus (i.e. the connection to the sur-rounding bone). Left untreated, such an injury could result in perilymphatic fistula of the RWM, requiring surgical intervention for associated hearing and vestibular symptoms. Furthermore as the RWM undergoes perforation it is deflected into the cochlea which increases the pressure within the cochlea. This pressure jump decreases with sharper needles because the deflection into the cochlea decreases.

In the course of our perforation experiments, the microneedles, while successfully fulfilling their purpose, have been blunted. This suggests that microneedles made of polymer will be for single use only, and that stronger materials may be preferred if similar geometries need to be used in the future to reduce damage to the tip. An SEM image of a post-perforation microneedle can be seen in FIG. 20, with the tip blunted to 2.5 to 3 µm in its radius of curvature.

Importantly, our results indicate that ultra-sharp needles with tips having 500 nm radius of curvature can perforate the RWM at extremely low forces, for example less than 1.6 mN. This low force minimizes the risk of trauma to the inner ear. Confocal examination of the RWM tissue surrounding the perforation revealed that fibers in the RWM tissue were separated along their axes without ripping or tearing of the RWM. This suggests that the main deformation mechanism to be fiber-to-fiber decohesion in the direction of the perforation major axis. That the minor axis does not close completely could be due to residual inelastic deformation induced by the needle or due to tensile prestrain in the membranes, or a combination of both. Such a growth mechanism is consistent with the notion that fibrous tissue strength is much weaker in the ground matrix perpendicular to the fibers than in the fiber directions. In addition, some fiber reorientation can be seen at the crack tip, which helps stabilize the crack against further propagation. With less sharp needles, the failure mechanism may change from a mode of fiber separation to one of fiber cutting, which would increase both trauma and the time necessary for the RWM to heal. From a manufacturing perspective, higher needle sharpness increases fabrication challenges and costs.

The shape of the RWM perforation may play a role in the delivery of therapeutics. Our results indicate that a final perforation has a major axis equal to that of the needle diameter and a minor axis approximately 25% of the needle diameter. The molecular size of the therapeutic should be smaller than the size of the minor axis if the therapeutic is to diffuse readily through the perforation.

Thus there are several medical and technical reasons to introduce very small RWM perforations. However a small perforation area limits the quantity of therapeutic that can be delivered into the cochlea in a given time period. The overall permeability of the perforated RWM can be increased by introducing multiple microperforations simultaneously across the RWM. FIG. 20 shows an array of seven microneedles that has been printed with the same methodology as described above for the single-needle array.

Not only can an array of microneedles increase the total area of perforation and therefore deliver a larger therapeutic dose, it can also improve the precision of the total perforation area and therapeutic dose. For the purposes of this discussion, accuracy or trueness of a dose is defined as the difference between the mean delivered dose and the prescribed dose. The precision of a dose quantifies the uncertainty of the delivered dose and therefore is proportional to the standard deviation of the delivered dose. Strictly speaking the precision is one-half of the width of the confidence interval of the true mean of the delivered dose. However since this quantity scales linearly with standard deviation, we will take standard deviation to be a proxy for precision herein. A reduction in the numerical value of standard deviation corresponds to an improvement in precision.

A single needle introducing perforations in a population of RWMs will yield perforations with mean area, $\mu_A$, and standard deviation, $\sigma_A$. The standard deviation can be normalized by the mean area to obtain the relative standard deviation $\sigma_A/\mu_A$ which will serve as a proxy for the relative precision. The relative precision is convenient because it expresses the precision as a proportion or percentage of the mean value.

We now assume an array of M identical microneedles spaced sufficiently far apart so that individual perforations introduced into a population of RWMs are not affected by their neighboring perforations. Thus each of the M perforations in each RWM will have mean area, $\mu_A$, and standard deviation, $\sigma_A$, that we will assume to be normally distributed.

It is well known that normally distributed random variables, say $X \sim N(\mu_X, \sigma^2)$ and $Y \sim N(\mu_Y, \sigma^2)$, with mean values $\mu_X$ and $\mu_Y$ as well as standard deviations $\sigma_X$ and $\sigma_Y$, respectively, have a sum $Z=X+Y$ written as $Z \sim N(\mu_X+\mu_Y, \sigma^2_X + \sigma^2_Y)$, where the functional representation N indicates the normal distribution. When applied to a population of RWMs perforated with an array of M microneedles, the sum of the total perforated area, $A_t$ can be expressed as $A_t \sim N(M\mu_A, M\sigma^2_A)$. In this case the relative standard deviation is $$\frac{\sqrt{M}\sigma A}{M \mu A} = \frac{1}{\sqrt{M}} \cdot \frac{\sigma A}{\mu A},$$

So the relative precision decreases in magnitude by the factor of $$\frac{1}{\sqrt{M}}$$

as M increases. Hence the relative precision improves by a factor of $\sqrt{M}$. By invoking concepts related to standard deviation of the means, we can obtain the same result even for non-normal distribution of the perforation areas.

For the case of M=7 needles shown in FIG. 13, we expect the relative precision of the total area to improve by a factor of $\sqrt{7} \approx 2.65$ that of the relative precision of a single perforation. Since the diffusion rate of a sufficiently small sized therapeutic is directly related to the area available for diffusion, we expect the relative precision of the dose to improve by the same factor.

As discussed above, the perforations in this study have mean area of $\mu A=1670$ $\mu m^2$ and standard deviation $\sigma_A=476$ $\mu m^2$, with a relative standard deviation of 0.285. If these statistics were to remain the same for an array of seven microneedles, the relative standard deviation would reduce to 0.108.

We now consider the design freedom enabled by the ease-of-use, flexibility and rapidity of 2PP and other related 3D printing fabrication methods. The needles need not be straight and need not have constant cross-sectional areas. Furthermore, the RWM surface is not planar and instead resembles a hyperbolic paraboloid. With the 2PP process, it is possible to fabricate arrays of microneedles in which each needle has individual characteristics to account for the non-planarity of the RWM. For example, In this study, there are certain limitations that will be addressed in future studies. The experimental setup does not allow measurement of lateral forces on microneedle during perforation. Such lateral forces play an important role in the potential failure mechanisms of the microneedles themselves, so it is important to quantify them under realistic conditions. In addition the material used in this study to fabricate the microneedles is not biocompatible, therefore a coating or the usage of another material will be pursued in future studies.

CONCLUSIONS

We report the use of direct 3D printing via Two-Photon Polymerization (2PP) lithography to fabricate ultra-sharp polymer microneedles specifically designed to perforate the guinea pig RWM.

The microneedle has tip radius of curvature of 500 nm and shank radius of 50 μm and perforates the guinea pig RWM with a mean force of 1.19 mN.

The resulting perforations performed in vitro are lens-shaped with major axis equal to the microneedle shank diameter and minor axis about 25% of the major axis, with mean area 1670 μm$^2$.

The major axis is aligned with the direction of the connective fibers within the RWM; the fibers were separated along their axes without ripping or tearing of the RWM suggesting the main failure mechanism to be fiber-to-fiber decohesion.

The small perforation area along with fiber-to-fiber decohesion are promising indicators that the perforations would heal readily following in vivo experiments.

The use of arrays of microneedles has the potential to improve the precision of a therapeutic dose as compared to delivery through a single microperforation.

These results establish a foundation for the use of Two-Photon Polymerization (2PP) lithography as a means to fabricate microneedles with extremely high accuracy and resolution to perforate the RWM and other similar membranes. The sharpness of microneedles achieved by two-photon lithography would be difficult to replicate using other standard micromanufacturing techniques. Finally, the 3D printing technology allows great design flexibility of needle design with respect to sharpness, cross-sectional properties, as well as the ability to fabricate non-straight microneedles.

While the work described herein focuses on accessing the cochlea, the technology can be translated to other anatomic barriers and enclosed spaces in the eye and central nervous system. Biodegradable ultra-sharp microneedles could be used to deliver therapeutic materials across the meninges into the brain and spinal cord, across the sclera into the eye and across the nerve sheath into peripheral nerves. Controlled therapeutic delivery without functional damage to these anatomic targets remains a challenge. The reservoirs used to house therapeutic materials for delivery can be modified for various pharmaceutical, molecular or cellular therapeutic agents depending on the clinical need.

What is claimed is:

1. A medical device comprising;
   a single microneedle comprising a longitudinal body having a maximum diameter from about 10 to about 150 microns and a detachable distal portion comprising a therapeutic agent; and
   a single tubular member coupled to a proximal end of the single microneedle, the tubular member capable of advancing the microneedle through an anatomic barrier.

2. The medical device of claim 1 wherein the anatomic barrier is a round window membrane of an inner ear.

3. The medical device of claim 1, wherein the single microneedle comprising a pinched region to facilitate cleavage of the detachable portion.

4. The medical device of claim 1, wherein the longitudinal body is hollow or solid.

5. The medical device of claim 1, wherein the microneedle comprises a tip having a tip radius of curvature of about 0.3 to 0.7 microns.

6. The medical device of claim 1, wherein the microneedle comprises a tip having a tip radius of curvature of about 2.5 to 3 microns.

7. The medical device of claim 1, wherein the tubular member is a syringe tip.

8. A medical device comprising;
   a single microneedle comprising a hollow longitudinal body having a maximum diameter from about 10 to about 150 microns and a detachable distal portion comprising a therapeutic agent, the distal portion having a tapered portion; and
   a single tubular member defining a lumen and coupled to a proximal end of the single microneedle, the tubular member connected to a reservoir for carrying a therapeutic agent for delivery through the lumen in the tubular member and the hollow longitudinal body of the microneedle, the tubular member capable of advancing the microneedle through an anatomic barrier.

9. The medical device of claim 8 wherein the anatomic barrier is a round window membrane of an inner ear.

10. The medical device of claim 8, the single microneedle comprising a pinched region to facilitate cleavage of the detachable portion.

11. The medical device of claim 8, wherein the longitudinal body comprises silicon or tungsten.

12. The medical device of claim 8, wherein the longitudinal body is configured with a taper along at least a portion of a length of the longitudinal body.

13. The medical device of claim 8, wherein the single microneedle comprises a pinched region to facilitate cleavage of the detachable portion.

14. The medical device of claim 8, wherein the tubular member is a syringe tip.

15. A medical device comprising;
   a single microneedle comprising a hollow longitudinal body having a maximum diameter from about 10 to about 150 microns and a detachable distal portion comprising a therapeutic agent, the distal portion having a tapered portion defining a taper of about 9 degrees, the single microneedle comprising a pinched region to facilitate cleavage of the detachable portion; and
   a single tubular member defining a lumen and coupled to a proximal end of the single microneedle, the tubular member connected to a reservoir for carrying a therapeutic agent for delivery through the lumen in the tubular member and the hollow longitudinal body of the microneedle, the tubular member capable of advancing the microneedle through an anatomic barrier.

16. The medical device of claim 15 wherein the anatomic barrier is a round window membrane of an inner ear.

17. The medical device of claim 15, wherein the longitudinal body comprises silicon or tungsten.

18. The medical device of claim 15, wherein the tubular member is a syringe tip.

19. The medical device of claim 18, wherein the tubular member is a gauge 23 syringe tip.

* * * * *